United States Patent
Sánchez Casals et al.

(10) Patent No.: US 12,331,053 B2
(45) Date of Patent: Jun. 17, 2025

(54) METHOD FOR OBTAINING AMORPHOUS REMIMAZOLAM BESYLATE

(71) Applicant: MOEHS IBERICA, S.L., Barcelona (ES)

(72) Inventors: Carles Sánchez Casals, Barcelona (ES); Alicia Dobarro Rodríguez, Barcelona (ES); Sergio Carneado Moreno, Barcelona (ES)

(73) Assignee: MOEHS IBERICA, S.L., Barcelona (ES)

( * ) Notice: Subject to any disclaimer, the term of this patent is extended or adjusted under 35 U.S.C. 154(b) by 770 days.

(21) Appl. No.: 17/627,275

(22) PCT Filed: Jul. 21, 2020

(86) PCT No.: PCT/EP2020/070528
§ 371 (c)(1),
(2) Date: Jan. 14, 2022

(87) PCT Pub. No.: WO2021/013826
PCT Pub. Date: Jan. 28, 2021

(65) Prior Publication Data
US 2022/0402923 A1     Dec. 22, 2022

(30) Foreign Application Priority Data
Jul. 22, 2019  (ES) .................... 201930677

(51) Int. Cl.
C07D 487/04     (2006.01)
(52) U.S. Cl.
CPC .................... *C07D 487/04* (2013.01)
(58) Field of Classification Search
CPC ...... C07D 487/04; A61K 9/19; A61K 9/0019; A61K 9/14
See application file for complete search history.

(56) References Cited

U.S. PATENT DOCUMENTS

| 9,193,730 B2 * | 11/2015 | Tilbrook | ............... A61P 25/00 |
| 2015/0224114 A1 * | 8/2015 | Kondo | .................. A61K 31/58 |
| | | | 540/562 |

FOREIGN PATENT DOCUMENTS

| EP | 1183243 B1 | 2/2006 |
| EP | 2852389 B1 | 10/2017 |
| WO | WO 2008/007071 A1 | 1/2008 |
| WO | WO 2013/029431 A1 | 3/2013 |
| WO | WO 2013/174883 A1 | 11/2013 |
| WO | WO-2017103550 A1 * | 6/2017 ............. A61K 35/37 |

OTHER PUBLICATIONS

American Laboratory, Freeze-Drying 101: Lyophilization Technology, Charles Dern, Apr. 4, 2005, https://web.archive.org/web/20130613032353/https://www.americanlaboratory.com/913-Technical-Articles/36127-Freeze-Drying-101-Lyophilization-Technology/ (Year: 2005).*

Ohori et al., Effects of Temperature Ramp Rate During the Primary Drying Process on the Properties of Amorphous-based lyophilized cake, Part 1: Cake Characterization, Collapse Temperature, and Drying Behavior, Journal of Drug Delivery Science and Technology, 39 (2017) 131-139 (Year: 2017).*

* cited by examiner

*Primary Examiner* — Noble E Jarrell
*Assistant Examiner* — Phillip Matthew Rzeczycki
(74) *Attorney, Agent, or Firm* — Casimir Jones, S.C.; Tristan Fuierer

(57) ABSTRACT

The present invention relates to a lyophilization method for obtaining amorphous remimazolam besylate without contamination of crystalline material of said product.

18 Claims, 21 Drawing Sheets

METHOD FOR OBTAINING AMORPHOUS REMIMAZOLAM BESYLATE

CROSS-REFERENCE TO RELATED APPLICATIONS

This application is filed under the provisions of 35 U.S.C. § 371 and claims the priority of International Patent Application No. PCT/EP2020/070528 filed on 21 Jul. 2020 entitled "METHOD FOR OBTAINING AMORPHOUS REMIMAZOLAM BESYLATE" in the name of Carles SÁNCHEZ CASALS, et al., which claims priority to Spanish Patent Application No. P201930677, filed on 21 Jul. 2019, both of which are hereby incorporated by reference herein in their entirety.

FIELD OF THE INVENTION

The present invention relates to a method for obtaining amorphous remimazolam besylate.

BACKGROUND OF THE INVENTION

Remimazolam, CNS 7056 or methyl 3-{(4S)-8-bromo-1-methyl-6-(pyridin-2-yl)-4H-imidazo[1,2-a][1,4]benzodiazepin-4-yl}propanoate, is a benzodiazepine developed by Paion having the following chemical structure:

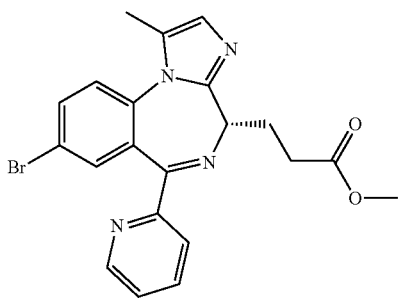 [SMILES: COC(=O)CC[C@@H]1N=C(c2ccccn2)c2cc(Br)ccc2-n2c(C)cnc21]

Remimazolam is a short-acting central nervous system depressant. It exhibits anxiolytic, amnestic, sedative, muscle relaxing, and anticonvulsant properties. Due to these properties, it is suitable for use in anesthetic practice and intensive care, such as in preoperative sedation, anxiolysis, amnestic use for perioperative cases, conscious sedation during short diagnostic, operative, or endoscopic procedures, for example, as a component for inducing and maintaining general anesthesia, before and/or along with the administration of other anesthetic agents, as well as in intensive care sedation. The most suitable administration of this compound is by intravenous route.

Patent EP 1 183 243 B1 discloses remimazolam and its preparation method in Example Ic-8.

Patent document WO 2008/007071 A1 discloses that remimazolam (in the form of free base) is stable when stored at 5° C., but behaves like a deliquescent solid when stored at 40° C. and 75% relative humidity (in an open vial) or at 60° C. and ambient humidity (in a closed vial), significantly reducing the initial remimazolam content and becoming yellow to orange in color. According to document WO 2008/007071 A1, the high-performance liquid chromatography (HPLC) study of remimazolam suggests that degradation occurs as a result of the formation of the impurity corresponding to the hydrolysis of methyl ester.

Document WO 2008/007071 A1 proposes solving said remimazolam storage stability problem by means of the formation of a besylate salt (benzenesulfonic acid salt) from said product in the form of a highly crystalline solid that can be readily isolated and has good thermal properties, low hygroscopicity, and good aqueous solubility. Document WO 2008/007071 A1 specifically discloses remimazolam monobesylate salt, wherein the molar ratio of benzenesulfonic acid and remimazolam is 1:1, in several crystalline forms designated as Form 1, Form 2, Form 3, and Form 4.

Document WO 2008/007071 A1 (Example 5) describes a remimazolam besylate polymorphism study in which the crystalline form 1 of the salt was subjected to maturation tests in fifteen different solvents and their corresponding aqueous mixtures. In most of the cases, either form 1 or an oil was obtained. Remimazolam besylate was only obtained in amorphous solid form when isopropanol, dichloromethane, or an aqueous THF solution was used. However, document WO 2008/007071 A1 does not include any data relating to the characterization of the amorphous form obtained or to its purity or stability. By reproducing the examples which, according to document WO 2008/007071 A1, yielded the amorphous form of remimazolam besylate, the present inventors did not obtain this solid form, but rather a crystalline form of the solid, specifically form 2.

Document EP 2 852 389 B1 relates to stable lyophilized benzodiazepine compositions including remimazolam. Said document explains that lyophilization is a known technique for stabilizing water-labile compounds. However, it also explains that lyophilizing remimazolam besylate alone (without excipients) did not result in satisfactory stability of said salt. Document EP 2 852 389 B1 proposes solving the problem relating to the lack of stability of remimazolam besylate by providing lyophilized compositions comprising a hygroscopic excipient and/or dextran, the lyophilized formulation being partially amorphous.

In the examples of document EP 2 852 389 B1, the crystalline material in a lyophilized formulation of remimazolam besylate and lactose monohydrate is evaluated. The studies performed on said formulation demonstrated the presence of crystalline material, specifically of remimazolam besylate salt in crystalline form, in this lyophilized formulation.

The main advantage of the products in amorphous solid form with respect to their crystalline equivalents is that they present improved solubility and bioavailability. However, their main drawback is that they are less stable than crystalline solids and develop into a crystalline form over time. The problem derived from the presence of crystalline remimazolam besylate in a matrix of amorphous remimazolam besylate is precisely that said amorphous compound does not remain stable when stored, but rather develops into one of the crystalline forms of besylate salt.

Therefore, there is a need in the state of the art for a method for preparing remimazolam besylate in amorphous form which allows obtaining said product without contamination of crystalline forms of besylate salt. The amorphous remimazolam besylate without contamination of crystalline forms is advantageous because it remains more stable when stored.

SUMMARY OF THE INVENTION

As shown in the examples, the inventors have performed several experiments in their attempt to obtain amorphous remimazolam besylate without contamination of the product in crystalline form, including various crystallization/precipitation tests with combinations of solvents and a variety of conditions, as well as spray-drying tests, without successfully obtaining the crystalline material-free amorphous product. Surprisingly, despite the unsatisfactory stability results described in document EP 2 852 389 B1 for lyophilized remimazolam besylate, the inventors have discovered a lyophilization method for preparing stable amorphous remimazolam besylate without contamination of the crystalline forms of said product.

To that end, in a first aspect the present invention relates to a method for preparing amorphous remimazolam besylate comprising the following steps:
  a) providing a solution consisting essentially of remimazolam besylate and a solvent selected from the group consisting of water-miscible organic solvent, water, and mixtures thereof, and
  b) lyophilizing the solution provided in step a), wherein the lyophilization comprises
    b1) freezing the solution provided in step a) at a temperature below −45° C., and
    b2) removing the solvent from the product obtained in step b1) by means of heating from the temperature of said product to a temperature of 10° C. to 40° C., at a pressure of less than 101325 Pa (1.01325 bar) and fora time period of less than 5 days.

In a second aspect, the present invention relates to stable amorphous remimazolam besylate, characterized in that it has an X-ray powder diffractogram presenting a broad peak between 10 and 40° 2θ±2°θ.

DETAILED DESCRIPTION OF THE INVENTION

Figure 1:
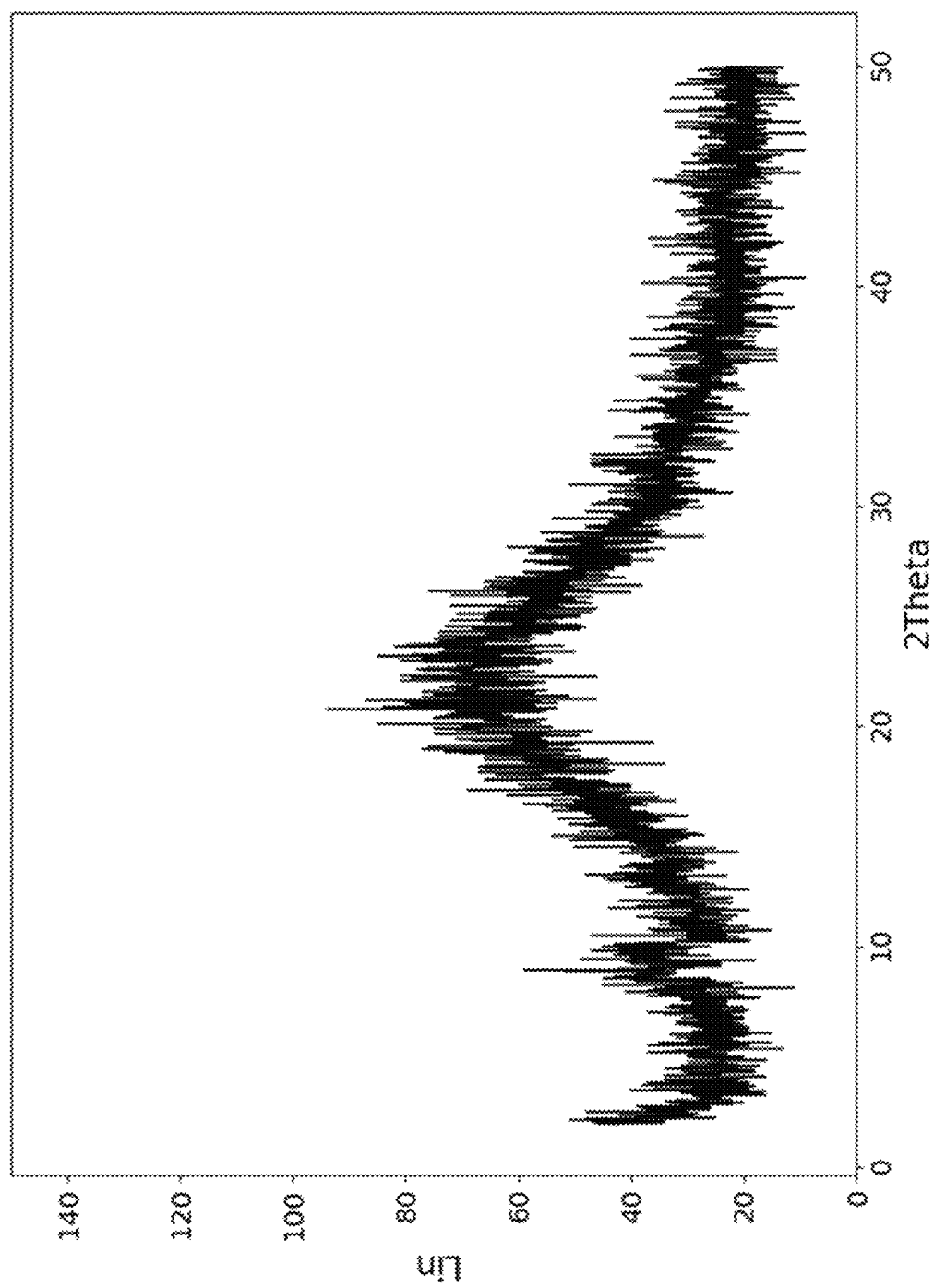
FIG. 1 shows the X-ray powder diffractogram (XRPD) of the remimazolam besylate obtained in Example 1.3.

In a first aspect, the present invention relates to a method for preparing amorphous remimazolam besylate comprising the following steps:
  a) providing a solution consisting essentially of remimazolam besylate and a solvent selected from the group consisting of water-miscible organic solvent, water, and mixtures thereof, and
  b) lyophilizing the solution provided in step a), wherein the lyophilization comprises
    b1) freezing the solution provided in step a) at a temperature below −45° C., and
    b2) removing the solvent from the product obtained in step b1) by means of heating from the temperature of said product to a temperature of 10° C. to 40° C., at a pressure of less than 101325 Pa (1.01325 bar) and fora time period of less than 5 days.

Remimazolam besylate refers to the salt of remimazolam and benzenesulfonic acid in a molar ratio of 1:1. To that end, the remimazolam besylate is a compound of formula (I):

In the context of the present invention, the term "amorphous" or "amorphous solid" refers to a solid state of matter, particularly of remimazolam besylate, in which the particles forming the solid lack an organized structure. These solids lack well-defined forms. This classification is in contrast to the classification of crystalline solids, the atoms of which are arranged in a regular and organized manner, forming crystalline lattices. In a crystalline solid, its atoms are arranged symmetrically. For that reason, its X-ray diffraction diagram shows several very well-defined peaks at specific angles. In an amorphous solid, the atoms are arranged randomly, so a small number of peaks, generally one, characterized by a large angular width, is observed in its diffraction diagram. Particularly, the amorphous remimazolam besylate is characterized by an X-ray powder diffractogram presenting a broad peak between 10 and 40°2θ±2°θ. The X-ray diffractogram can be recorded using a powder diffraction system with a copper anode which emits CuKα radiation with a wavelength of 1.541838 Å, particularly following the method described in the examples.

The expression "crystalline remimazolam besylate" refers to remimazolam besylate in the form of crystalline solid, i.e., in which the atoms are arranged in a regular and organized manner, forming crystalline lattices. To that end, the X-ray diffraction diagram of the crystalline forms shows several very well-defined peaks at specific angles. Particularly, crystalline remimazolam besylate refers to form 1, form 2, form 3, and form 4 defined in document WO 2008/007071 A1.

In the context of the present invention, the expression "a solution consisting essentially of remimazolam besylate and a solvent" is used to characterize solutions in which the sum of the amounts by weight of remimazolam besylate and of the solvent represent at least 95%, more preferably at least 97%, more preferably at least 99%, more preferably at least 99.5%, and more preferably at least 99.9% by weight of the solution.

The method of the present invention allows obtaining amorphous remimazolam besylate that is stable over time due to the absence of crystalline forms. Said stability refers to the product not developing into crystalline forms when stored, particularly when stored at 40° C. and 80% relative humidity and/or when stored at 25° C. and 60% relative humidity for at least 15 days, preferably for at least 30 days, more preferably when stored for at least 15 days at 40° C. and 80% relative humidity, even more preferably for at least 30 days and most preferably for at least 6 months. The presence/absence of crystalline forms can be determined by means of X-ray powder diffraction analysis, particularly using a powder diffraction system with a copper anode which emits CuKα radiation with a wavelength of 1.541838 Å, following the experimental protocol described in the examples. Particularly, the amorphous remimazolam besylate is characterized by an X-ray powder diffractogram presenting a broad peak between 10 and 40°2θ±2°θ, whereas the X-ray diffraction diagram of the crystalline forms shows several very well-defined peaks at specific angles, particularly according to the X-ray powder diffractograms shown in document WO 2008/007071 A1 for crystalline remimazolam besylate form 1, form 2, form 3, and form 4.

The first step of the method of the invention, step a), is providing a solution consisting essentially of remimazolam besylate and a solvent selected from the group consisting of water-miscible organic solvent, water, and mixtures thereof.

Any form of remimazolam besylate, either an amorphous solid or a crystalline solid, such as those designated as Form 1, Form 2, Form 3, and Form 4 in document WO 2008/007071 A1, as well as mixtures of any of said solid forms, can be used. This document also describes the method for obtaining said crystalline forms. Preferably, in step a) of the present invention Form 1 (as designated in document WO 2008/007071 A1) of remimazolam besylate is used.

The solvent used for the solution of step a) is selected from the group consisting of water-miscible organic solvent, water, and mixtures thereof.

The expression "water-miscible organic solvent" refers to a carbon-containing liquid compound which, when mixed with water in any ratio at a temperature between 20 and 25° C., leads to the attainment of a mixture having a single liquid phase. Examples of organic water-miscible solvents are acetonitrile, dimethylsulfoxide, methanol, ethanol, and isopropanol, preferably acetonitrile.

The mixtures of solvents may have two or more solvents, such as for example, 2, 3, or 4 solvents, preferably two solvents, more preferably wherein one of the solvents of the mixture is water or acetonitrile, even more preferably wherein one of the solvents of the mixture is water. The solvents of the mixture can be in any volumetric ratio with respect to one another. Particularly, when mixtures of water and another solvent selected from acetonitrile and dimethylsulfoxide are used the water content is at least 5% by volume. Particularly, when mixtures of water and another solvent selected from methanol, ethanol, and isopropanol are used, the water content is at least 70% by volume.

Preferably, the solvent of step a) is selected from the group consisting of water, acetonitrile, and mixtures thereof, more preferably the solvent is water.

In the mixtures of water and acetonitrile, said solvents can be in any volumetric ratio with respect to one another, for example in a water:acetonitrile volume ratio of 0.1:1 to 10:1, preferably 0.2:1 to 5:1, more preferably 0.25:1 to 4:1, more preferably 0.3:1 to 3:1, more preferably 0.5:1 to 2:1, more preferably 0.6:1 to 1.5:1, more preferably 0.8:1 to 1.2:1, even more preferably 0.9:1 to 1.1:1, most preferably 1:1.

More preferably, the solvent of step a) is selected from the group consisting of water, acetonitrile, and a mixture of water and acetonitrile in a volume ratio of 0.5:1 to 2:1.

In a particular embodiment, the concentration of remimazolam besylate in the solution provided in step a) is from 5 to 15 mg/mL (mg of remimazolam besylate/mL of solution), more preferably 7 to 13 mg/mL.

The next step of the method of the invention, step b), is lyophilizing the solution provided in the preceding step, step a).

The term "lyophilize" or "lyophilization" refers to a process the purpose of which is to separate water, an organic solvent, or a mixture thereof from a solution which, in the present invention, contains remimazolam besylate as solute, by means of freezing the solution and then sublimating the frozen solvent (solid). The term "sublimation" or "sublimate" refer to the process of changing from solid state to gaseous state without going through liquid state. Lyophilization involves a step of freezing the solution below its eutectic point (which is the minimum temperature at which all the components of the solution freeze) and a step of sublimating the solvent (water, organic solvent, or mixture thereof) of the frozen product and removing the sublimated solvent. Generally, solvent sublimation and removal is performed at a reduced pressure, i.e., pressure of less than 101325 Pa.

The lyophilization step b) of the method of the present invention comprises:
- b1) freezing the solution provided in step a) at a temperature below −45° C., and
- b2) removing the solvent from the product obtained in step b1) by means of heating from the temperature of said product to a temperature of 10° C. to 40° C., at a pressure of less than 101325 Pa (1.01325 bar), and for a time period of less than 5 days.

Step b1) of freezing the solution provided in step a) at a temperature below −45° C. can be performed by cooling the solution of step a) at a temperature below −45° C., for example by means of using liquid nitrogen or a mixture of dry ice (solid $CO_2$) and acetone, until the solution freezes completely.

In a preferred embodiment, the freezing temperature of step b1) is below −55° C., preferably the freezing temperature of step b1) is from −55° C. to −85° C., more preferably from −55° C. to −65° C. or from −75° C. to −85° C., even more preferably from −58° C. to −62° C. or from −78° C. to −82° C.

Preferably, the temperature of step b1) is maintained for 10 minutes to 36 hours, more preferably 10 minutes to 1 hour or 15 hours to 30 hours, even more preferably 10 minutes to 40 minutes or 20 hours to 25 hours.

Preferably, the freezing temperature of step b1) is from −55° C. to −65° C. and is maintained at this temperature range for 15 hours to 30 hours, or wherein the freezing temperature of step b1) is from −75° C. to −85° C. and is maintained at this temperature range for 10 minutes to 1 hour.

Preferably, the freezing temperature of step b1) is from −58° C. to −62° C. and is maintained at this temperature range for 20 hours to 25 hours, or wherein the freezing temperature of step b1) is −78° C. to −82° C. and is maintained at this temperature range for 10 minutes to 40 minutes.

Once step b1) has ended, the next step of the lyophilization, step b2), is performed in which the solvent (water, water-miscible organic solvent, or mixture thereof as defined above) is removed from the product obtained (frozen) in step b1) by means of heating from the temperature of said product to a temperature of 10° C. to 40° C., at a pressure of less than 101325 Pa (1.01325 bar), and for a time period of less than 5 days. The term "remove" means completely or partially reducing the solvent content of the frozen product obtained in step b1). Said solvent removal yields a product having a solvent content of less than 5%, preferably a solvent content of less than 3% by weight, more preferably less than 2% by weight, more preferably less than 1% by weight, more preferably less than 0.5% by weight, wherein the percentage by weight is the weight of the solvent present in the product obtained after step b2) with respect to the total weight of the product obtained in step b2). The percentage of solvent present in the product obtained in step b2) can be determined by means of thermogravimetric analysis or by means of Karl-Fischer volumetric titration analysis.

The method for determining the percentage of solvent present in the product obtained in step b2) by means of thermogravimetric analysis can be performed using a thermobalance (for example, Mettler Toledo model TGA/SDTA851e) arranging the sample to be analyzed in a 70-microliter alumina crucible with a nitrogen flow of 50 mL/min over the sample. The sample is heated from 30 to 300° C. with a temperature increase by means of 10° C./min gradient. Before analyzing the sample, a blank, which is subtracted from the sample analysis result, is performed under the same conditions.

Alternatively, the method for determining the percentage of solvent present in the product obtained in step b2) when said solvent is water can also be performed by means of Karl-Fischer titration analysis. In this case, a volumetric titrator (for example, Mettler Toledo model V30) can be used, arranging the accurately-weighed sample to be analyzed in the titration beaker and performing titration with the corresponding reagent having a known mg/mL concentration (for example, Hydranal Composite 5K) until reaching the titration end point.

Preferably, the pressure in step b2) is from 0.01 Pa (0.0001 mbar) to 101000 Pa (1.01 bar), more preferably the pressure in step b2) is from 0.01 Pa (0.0001 mbar) to 100 Pa (1 mbar) or 50000 Pa (0.5 bar) to 101000 Pa (1.01 bar), even more preferably the pressure in step b2) is from 0.05 Pa (0.0005 mbar) to 50 Pa (0.5 mbar) or from 90000 Pa (0.9 bar) to 101000 Pa (1.01 bar).

Preferably, the heating in step b2) is performed until a temperature of 15 to 30° C., more preferably until a temperature of 20 to 25° C.

Preferably, the temperature variation in step b2) of the method of the invention is from 0.5 to 1.5° C./minute, more preferably from 0.8 to 1.2° C./min, even more preferably from 0.9 to 1.1° C./min.

Step b2) is performed until the complete removal of all the solvent, with the proviso that it has a duration of less than 5 days. Preferably, step b2) is performed for a time period of less than 4 days, more preferably less than 3 days, more preferably 20 to 60 hours, even more preferably 20 to 30 hours or 40 to 60 hours.

In a preferred embodiment, step b2) is performed at a pressure of 50000 Pa (0.5 bar) to 101000 Pa (1.01 bar) for a time period of 20 to 30 hours, more preferably at a pressure of 90000 Pa (0.9 bar) to 101000 Pa (1.01 bar) for a time period of 20 to 30 hours.

In a particular embodiment, the freezing temperature of step b1) is from −75° C. to −85° C. and is maintained in this temperature range for 10 minutes to 1 hour, and step b2) is performed at a pressure of 50000 Pa (0.5 bar) to 101000 Pa (1.01 bar) for a time period of 20 to 30 hours, with heating to a temperature from 15 to 30° C.

In another preferred embodiment, step b2) is performed at a pressure of 0.01 Pa (0.0001 mbar) to 100 Pa (1 mbar) for a time period of 40 to 50 hours, more preferably at a pressure of 0.05 Pa (0.0005 mbar) to 50 Pa (0.5 mbar) for a time period of 40 to 50 hours.

In a particular embodiment, the freezing temperature of step b1) is from −55° C. to −65° C. and is maintained at this temperature range for 20 to 30 hours, and step b2) is performed at a pressure of 0.01 Pa (0.0001 mbar) to 100 Pa (1 mbar) for a time period of 40 to 50 hours, with heating to a temperature of 15 to 30° C., more preferably to a temperature of 15 to 25° C.

Preferably, step b2) of the method of the invention comprises:
- (i) maintaining a temperature of −30° C. to −20° C. and a pressure of 10 Pa (0.1 mbar) to 50 Pa (0.5 mbar) for a time period of 15 to 24 h,
- (ii) maintaining a temperature of −5° C. to 5° C. and a pressure of 10 Pa (0.1 mbar) to 50 Pa (0.5 mbar) for a time period of 6 to 18 h,
- (iii) maintaining a temperature of 8° C. to 15° C. and a pressure of 10 Pa (0.1 mbar) to 50 Pa (0.5 mbar) for a time period of 12 to 24 h, and (iv) maintaining a temperature of 15° C. to 25° C. and a pressure of 0.01 Pa (0.0001 mbar) to 1 Pa (0.01 mbar) for a time period of 3 to 18 h.

Particularly, steps (i)-(iv) are performed sequentially, i.e., first step (i) is performed, then step (ii), then step (iii), and finally step (iv).

In a particular embodiment, the freezing temperature of step b1) is from −55° C. to −65° C. and is maintained in this temperature range for 20 to 30 hours, and step b2) comprises steps (i)-(iv) described above.

Preferably, the temperature variation in step b2) of the method of the invention is from 0.5 to 1.5° C./minute, more preferably from 0.8 to 1.2° C./min, even more preferably from 0.9 to 1.1° C./min.

In a preferred embodiment, the lyophilization of step b) of the method of the invention is carried out in the absence of a hygroscopic excipient selected from the group consisting of lactose, mannitol, trehalose, sucrose, maltose, dextran, povidone, glycine, and mixture thereof, i.e., the mentioned hygroscopic excipients are not present in the remimazolam besylate solution provided in step a), frozen in step b1), and treated in step b2).

In a particular embodiment, the lyophilization of step b) of the method of the invention is carried out in the absence of a hygroscopic excipient selected from the group consisting of carbohydrates and/or organic polymers.

The term "carbohydrate" refers to an organic compound of empirical formula $C_m(H_2O)_n$. Structurally, carbohydrates can be described as polyhydroxylated ketones and aldehydes. Carbohydrates are divided into four chemical groups: monosaccharides, disaccharide, oligosaccharides, and polysaccharides. The carbohydrates defined herein include all the carbohydrate modifications, derivatives, and analogs such as acidic saccharides containing carboxyl groups, phosphate groups, and/or sulfuric ester groups. Examples of carbohydrates are amylose, amylopectin, alginate, dextrans, starches, mono-, di-, and oligosaccharides. Examples of disaccharides are lactose, maltose, sucrose, and trehalose. Examples of polysaccharides are dextrans. The organic polymer is preferably a polyacrylate or vinyl polymer, more preferably polyvinylpyrrolidone (or povidone)

The lyophilization can be carried out in a lyophilizer, which is an apparatus generally comprising the following elements: a dry chamber, a condenser with a cooling circuit, and a vacuum system.

The dry chamber or lyophilization chamber is the place where the solution to be lyophilized is placed. It may have different shapes with compartments where sublimation is performed, with the water going from solid to vapor. The closure is hermetic and it operates at a reduced pressure.

The condenser with a cooling circuit communicates with the dry chamber and it is where vapor that is being produced during sublimation condenses. A coolant keeps it at a lower temperature than the dry chamber (generally between −50 and −125° C.).

The vacuum system produces vacuum (reduced pressure, i.e., pressure of less than 101325 Pa) with an oil pump which operates connected to a trap so that vapors from the solvent do not enter same. The vacuum system first removes air from the dry chamber when the lyophilization process is started, and then helps in sublimation.

The lyophilizer also comprises a temperature regulation system which allows reaching the desired freezing temperatures of the product to be lyophilized, as well as a temperature regulation system which allows reaching up to at least 40° C.

Figure 2:
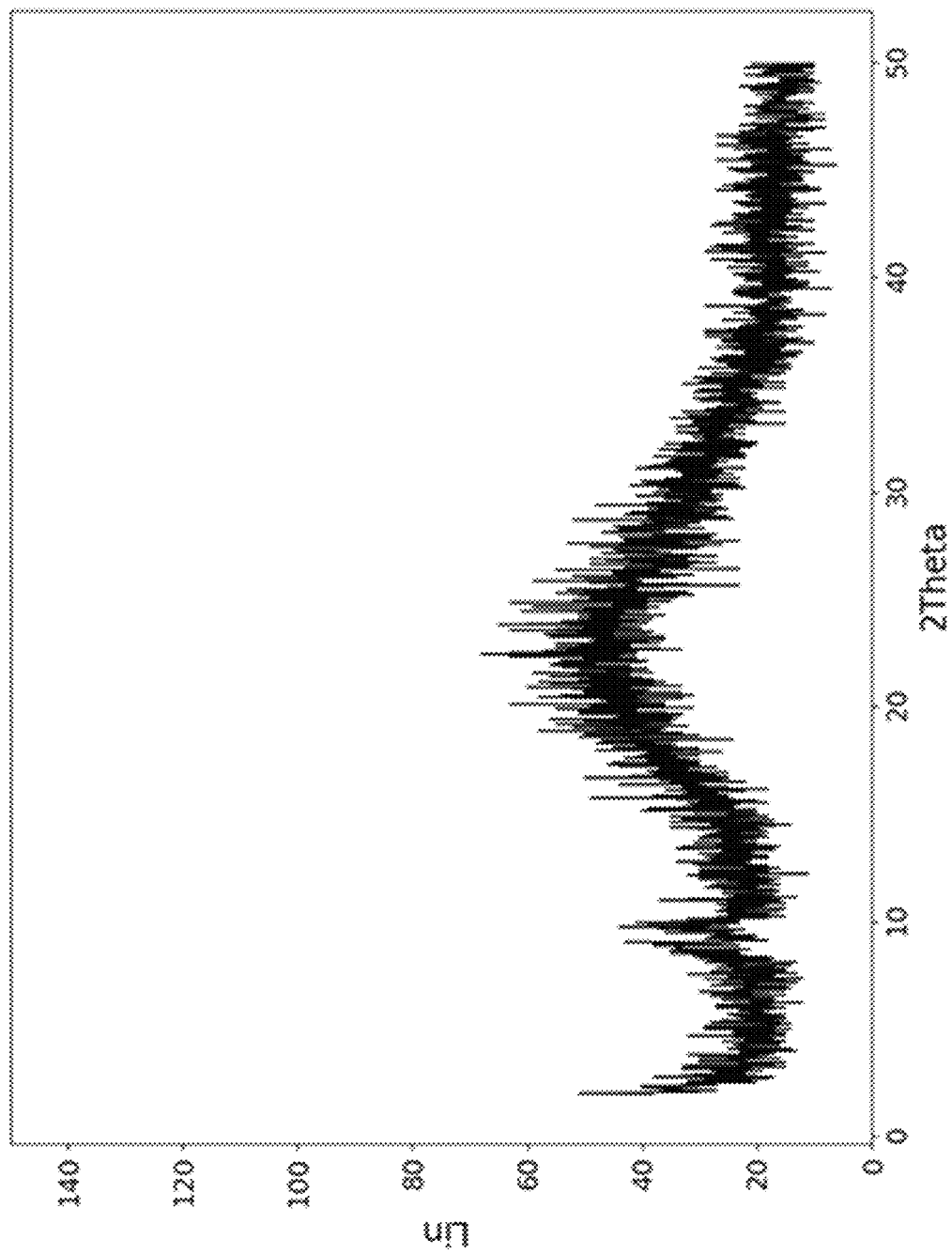
FIG. 2 shows the X-ray powder diffractogram (XRPD) of the remimazolam besylate obtained in Example 1.5.
Figure 3:
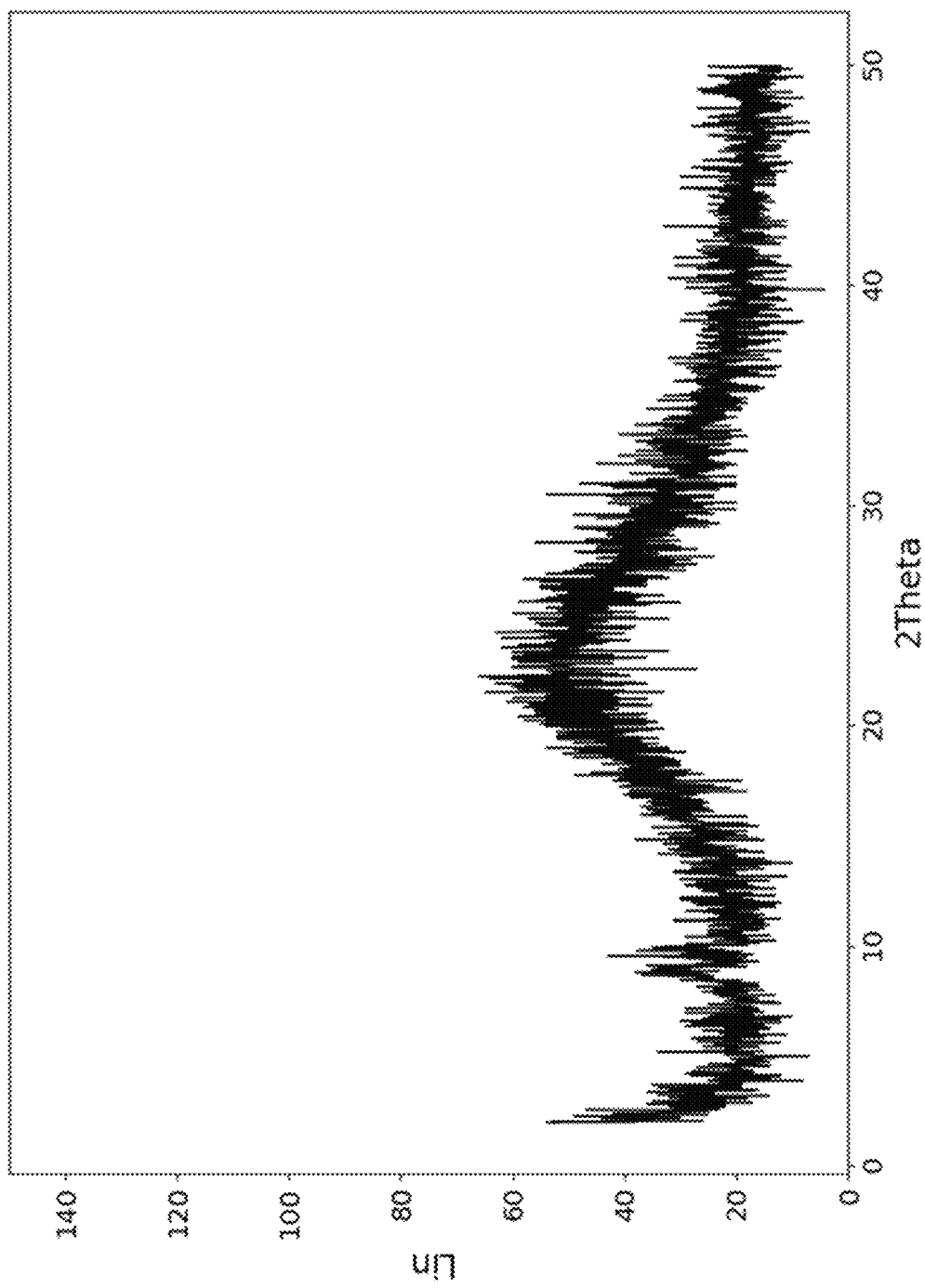
FIG. 3 shows the X-ray powder diffractogram (XRPD) of the remimazolam besylate obtained in Example 1.6.

An additional aspect of the present invention relates to stable amorphous remimazolam besylate characterized by an X-ray powder diffractogram presenting a broad peak between 10 and 40°2θ±2°θ, preferably an X-ray powder diffractogram substantially like the one shown in FIG. 1, 2, or 3.

The term "stable" refers to the amorphous remimazolam besylate not developing into crystalline forms when stored, particularly when stored at 40° C. and 80% relative humidity and/or when stored at 25° C. and 60% relative humidity for at least 15 days, preferably for at least 30 days, more preferably when stored for at least 15 days at 40° C. and 80% relative humidity, even more preferably for at least 30 days and most preferably for at least 6 months.

The presence/absence of crystalline forms can be determined by means of X-ray powder diffraction analysis, particularly using a powder diffraction system with a copper anode which emits CuKα radiation with a wavelength of 1.541838 Å, following the experimental protocol described in the examples. Particularly, the amorphous remimazolam besylate is characterized by an X-ray powder diffractogram presenting a broad peak between 10 and 40°2θ±2°θ, whereas the X-ray diffraction diagram of the crystalline forms shows several very well-defined peaks at specific angles, particularly according to the X-ray powder diffractograms shown in document WO 2008/007071 A1 for crystalline remimazolam besylate form 1, form 2, form 3, and form 4.

Preferably, the stable amorphous remimazolam besylate is characterized by an X-ray diffractogram with the absence of peaks characteristic of crystalline form 1, i.e., the absence of peaks at 7.3, 7.8, 9.4, 12.1, 14.1, 14.7, and/or 15.6°2 θ±0.2°, the absence of peaks characteristic of crystalline form 2, i.e., the absence of peaks at 8.6, 10.5, 12.0. 13.1, 14.4 15.9, and/or 16.2°2 θ±0.2°, the absence of peaks characteristic of crystalline form 3, i.e., the absence of peaks at 7.6, 11.2, 12.4, 14.6, 15.2, 16.4, and/or 17.7° 2θ±0.2°, and the absence of peaks characteristic of crystalline form 4, i.e., the absence of peaks at 7.6, 10.8, 15.2, 15.9, and/or 22.0° 2θ±0.2°.

The present invention also relates to the amorphous remimazolam besylate that can be obtained by means of the lyophilization method of the first aspect described above.

To facilitate understanding the preceding ideas, some examples of the experimental methods and embodiments of the present invention are described below. Said examples are merely illustrative.

EXAMPLES

Methods of Analysis

The XRPD analysis was performed using a Siemens model D-5000 X-ray powder diffractometer equipped with a copper anode. The radiation used is CuKα with a wavelength of 1.541838 Å. Scanning parameters: 4-50 degrees 2θ, continuous scan, ratio: 1.2 degrees/minute.

The differential scanning calorimetry (DSC) analysis was performed in a Mettler Toledo 822e apparatus with STARe SW15.00 software. Parameters: range of heating from 25 to 300° C. with a ramp of 20° C./min and a $N_2$ flow of 50 mL/min. The measurement was taken with a closed perforated capsule.

The thermogravimetric analysis for obtaining the percentage by weight of water was performed in a Mettler Toledo TGA/STDA851e thermobalance using about 3 mg of sample to be analyzed and a nitrogen flow of 50 mL/min. The sample was heated from 30 to 300° C. with a ramp of 10°

C./min. A blank was first performed under the same conditions of analysis and subtracted from the result obtained for the sample.

The purity of the products obtained was analyzed by means of the ultra-high performance liquid chromatography (UHPLC) technique in a Waters brand Acquity model apparatus provided with a photodiode detector and thermostatic oven for the column. A CSH C18 (3×50 mm and 1.7 μm) column and mobile phases A ($KH_2PO_4$ 5 mM pH 2) and B (acetonitrile) were used with the following conditions of analysis:

Flow rate: (mL/min): 0.5

Column T (° C.): 40

Wavelength (nm): 230

Injection volume (μL): 1

Acquisition time (min): 10

Diluent: acetonitrile/water (1:1)

Gradient:

| t (min) | % A | % B |
|---|---|---|
| 0 | 80 | 20 |
| 0.5 | 80 | 20 |
| 7.5 | 40 | 60 |
| 8.5 | 40 | 60 |
| 9 | 80 | 20 |
| 10 | 80 | 20 |

Example 1. Obtaining Amorphous Remimazolam Besylate by Means of Lyophilization

Remimazolam besylate obtained by means of the method disclosed in Example 7 of document WO2019/072944 Å, which corresponds to Form 1, has been used as starting material in the lyophilization tests.

The lyophilization assays were performed either in a Telstar brand LyoQuest series lyophilizer (protocol A) or in a Telstar brand LyoBeta 35 series lyophilizer (protocol B).

In protocol A, the freezing temperature was −80° C. The drying time was 24 hours, during which the temperature was allowed to go from −80° C. to 25° C. The temperature variation ramp was 1° C./min. The vacuum pressure during drying was 100000 Pa (1.0 bar).

In protocol B, the freezing temperature was −60° C. The drying time was divided into primary drying (18 hours at −25° C., 8 h at 0° C., and 15 hours at 10° C.) and secondary drying (5 hours at 20° C.). The temperature variation ramps were established at 1° C./min. The vacuum pressure during drying was 20 Pa (0.2 mbar) during primary drying and 0.1 Pa (0.001 mbar) during secondary drying.

The resulting solid in each of the tests was kept under $N_2$ atmosphere.

The particular conditions of assays 1.1-1.5, as well as the results obtained are shown in Table 1, in which RM refers to remimazolam and RM-acid refers to the carboxylic acid product obtained by means of remimazolam methyl ester hydrolysis. The solvent used, the concentration of remimazolam besylate in the solution, and the solution volume are indicated in the solvent column.

TABLE 1

| Assay | Protocol | Solvent | Freezing time | Solid form | UHPLC |
|---|---|---|---|---|---|
| 1.1 | A | water 7.5 mg/mL (10 mL) | 15 minutes | amorphous | 99.39% RM 0.24% RM-acid |
| Assay | Protocol | Solvent | Freezing time | Solid form | UHPLC |
| 1.2 | A | acetonitrile 10 mg/mL (10 mL) | 30 minutes | amorphous | 99.42% RM 0.23% RM-acid |
| 1.3 | A | acetonitrile/ water 50:50 10 mg/mL (10 mL) | 30 minutes | amorphous (FIG. 1) | 98.98% RM 0.74% RM-acid |
| 1.4 | A | water 10 mg/mL (10 mL) | 15 minutes | amorphous | 99.44% RM 0.22% RM-acid |
| 1.5 | B | acetonitrile 12.3 mg/mL (13 mL) | 23 hours | amorphous (FIG. 2) | 99.70% RM 0.14% RM-acid |
| 1.6 | B | water 7.5 mg/mL (10 mL) | 23 hours | amorphous (FIG. 3) | 99.67% RM 0.17% RM-acid |

In all the assays that were performed, the amorphous form of remimazolam besylate salt was obtained, without detecting the presence of any crystalline form, be it Form 1, Form 2, Form 3, or Form 4 described in document WO 2008/007071 A1. Additionally, in the assays using protocol B and water as solvent, the amorphous form of remimazolam besylate salt with a water content varying between 0.1% and 0.4% by weight was obtained. Particularly, in assay 1.6 a percentage of water corresponding to 0.22% was obtained.

Comparative Example 2. Attempt to Obtain Amorphous Form by Means of Precipitation Remimazolam besylate obtained by means of the method disclosed in Example 7 of document WO2019/072944 Å, which corresponds to Form 1, has been used as starting material in the precipitation tests.

Different precipitation tests were performed in an attempt to obtain the amorphous form of remimazolam besylate following method protocols C, D, and E, as described below:

Protocol C: xg of remimazolam besylate were dissolved in the amount of solvent or mixture of solvents indicated in Table 2 (1 Vol refers to 1 mL of the corresponding solvent per 1 mg of initial remimazolam besylate) at a temperature of about 50° C. The solution thus obtained was added to the antisolvent previously heated to a temperature of about 50° C. A precipitated solid was observed almost immediately and the mixture thus obtained was cooled to a temperature of about 0° C. The resulting solid in each of the tests was filtered and dried in an oven, being stored under $N_2$ atmosphere until the XRPD analysis thereof.

Protocol D: xg of remimazolam besylate were dissolved in the amount of solvent or mixture of solvents indicated in Table 2 (1 Vol refers to 1 mL of the corresponding solvent per 1 mg of initial remimazolam besylate) at a temperature of about 50° C. The solution thus obtained was added to the antisolvent previously cooled to a temperature of about 0° C. A precipitated solid was observed almost immediately (with the exception of assay 10) and the mixture thus obtained was kept for 30 minutes at a temperature of about 0° C. The resulting solid in each of the assays was filtered and dried in an oven, being stored under $N_2$ atmosphere until the XRPD analysis thereof.

Protocol E: xg of remimazolam besylate were dissolved in the amount of solvent or mixture of solvents indicated in Table 2 (1 V or 1 Vol refers to 1 mL of the corresponding solvent per 1 mg of initial remimazolam besylate) at a temperature of about 20° C. The solution thus obtained was added to the antisolvent previously cooled to a temperature of about 0° C. A precipitated solid was observed almost immediately and the mixture thus obtained was kept for 30 minutes at a temperature of about 0° C. The resulting solid in each of the assays was filtered and dried in an oven, being stored under $N_2$ atmosphere until the XRPD analysis thereof.

The particular conditions of assays 2.1-2.14 as well as the results obtained are shown in Table 2.

TABLE 2

| Assay | Solvent | Antisolvent | Protocol | XRPD |
|---|---|---|---|---|
| 2.1 | methanol 3 V | isopropyl acetate 50 V | C | Form 2 |
| 2.2 | acetone 2 V/water 0.5 V | n-heptane 100 V | C | Form 1 |
| 2.3 | isopropanol 2 V/water 0.5 V | n-heptane 100 V | C | Form 1 |
| 2.4 | acetonitrile 2 V/water 0.25 V | n-heptane 100 V | C | Form 1 |
| 2.5 | methanol 2 V | n-heptane 100 V | C | Form 1 |
| 2.6 | isopropanol 2 V/water 0.5 V | isopropyl acetate 100 V | C | Form 1 |
| 2.7 | acetonitrile 2 V/water 0.5 V | isopropyl acetate 200 V | C | Form 1 |
| 2.8 | isopropanol 2 V/water 0.5 V | isopropyl acetate 200 V | D | Form 1 |
| 2.9 | acetonitrile 2 V/water 0.5 V | isopropyl acetate 200 V | D | Form 1 + Form 2 |
| 2.10 | acetonitrile 2 V/water 0.5 V | water 200 V | D | No solid |
| 2.11 | acetonitrile 2.5 V/water 0.25 V | n-heptane 200 V | D | Form 1 |
| 2.12 | isopropanol 2.5 V/water 0.5 V | n-heptane 200 V | D | Form 2 + Form |
| 2.13 | glacial acetic acid 4 V/water 0.5 V | n-heptane 200 V | E | Form 1 |
| 2.14 | acetonitrile 2.5 V/water 0.5 V | methyl-tert-butyl ether 100 V | E | Form 1 |

TABLE 3

| Assay | Feed flow rate (ml/min) | Compressed air flow rate (l/h) | Inlet T (° C.) | Outlet T (° C.) | Solvent (weight in g) | Initial amount of remimazolam besylate (g) |
|---|---|---|---|---|---|---|
| 3.1 | 10.4 | 473 | 84 | 42-44 | acetonitrile (266) | 4.0 |
| 3.2 | 12.9 | 536 | 70 | 23 | methanol (166) | 4.0 |
| 3.3 | 29.5 | 819 | 65 | 21-23 | methanol (150) | 3.0 |
| 3.4 | 29.5 | 536 | 65 | 19-23 | methanol (623) | 4.1 |

As can be observed, none of the tests yielded the amorphous form of remimazolam besylate. A solid was not obtained in one of the assays (assay 2.10), and either form 1 or form 2 described in document WO 2008/007071 A1 was obtained in the other assays (assays 2.1-2.9 and 2.11-2.14).

Comparative Example 3. Attempt to Obtain Amorphous Form by Means of Spray-Drying The spray-drying tests were performed in a Büchi B-290 equipment which allows air inlet temperatures of up to 220° C., maximum air flow rates of 35 m³/h, and a maximum compressed air flow rate of 800 L/h. The system consists of a closed circuit, in which a dehumidifier and a solvent condenser are intercalated between the drying air inlet and outlet of the spraying equipment. The air circuit was initially filled with nitrogen and spraying of the feed mixture was started in the moment in which oxygen practically disappears from the circuit.

Different experimental tests were performed using methanol or acetonitrile as solvents, different compressed air flow rates (L/h), and different inlet and outlet temperatures (° C.). The drying air flow rate was kept constant at 38 m³/h in all the assays.

Remimazolam besylate obtained by means of the method disclosed in Example 6 of document WO2019/072944 Å, which corresponds to Form 1, has been used as starting material in the spray-drying assays.

The particular conditions of the performed assays (assays 3.1-3.4) as well as the results obtained are shown in Table 3.

Figure 4:
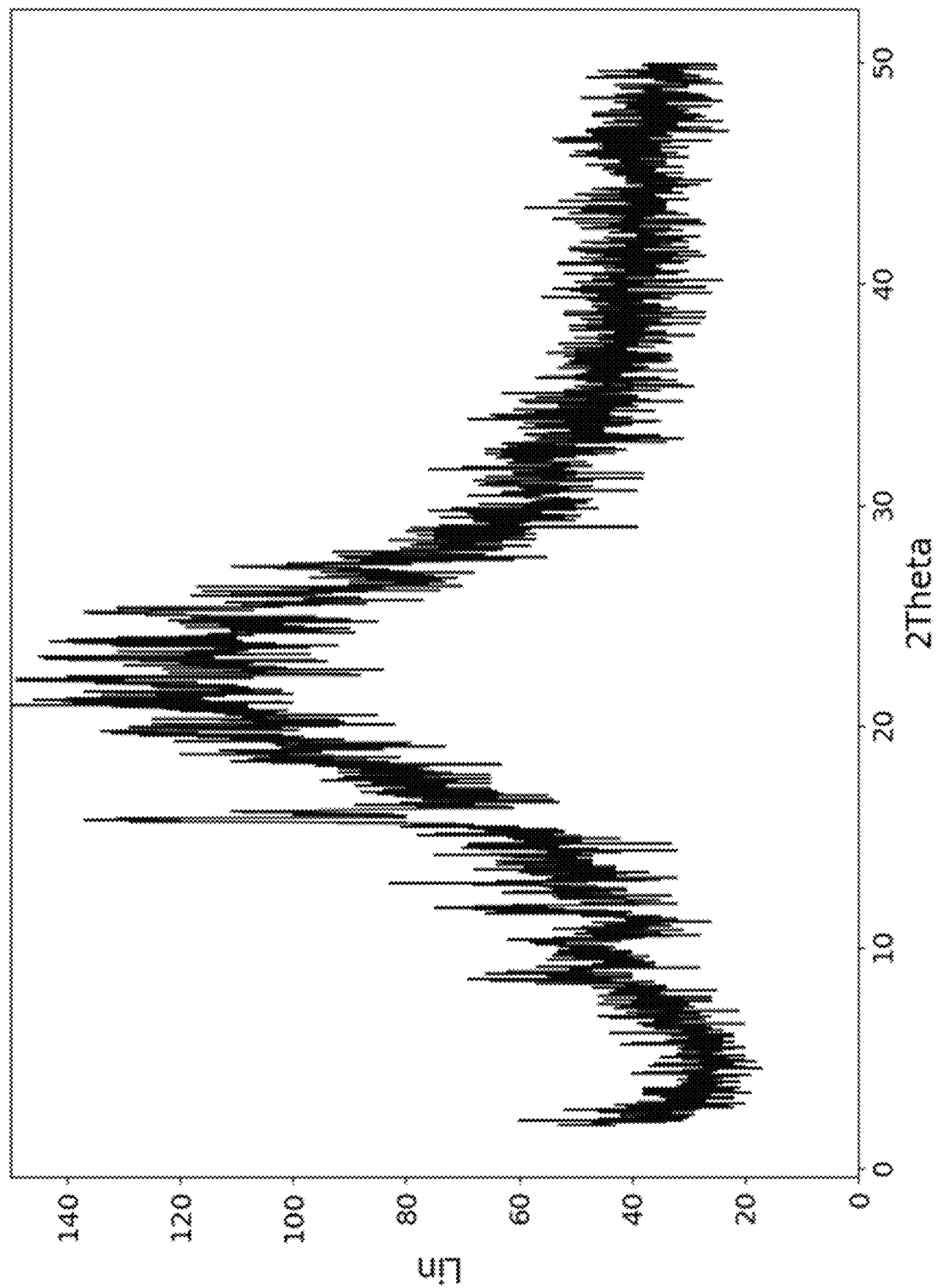
FIG. 4 shows the X-ray powder diffractogram (XRPD) of the remimazolam besylate obtained in Comparative Example 3.
Figure 5:
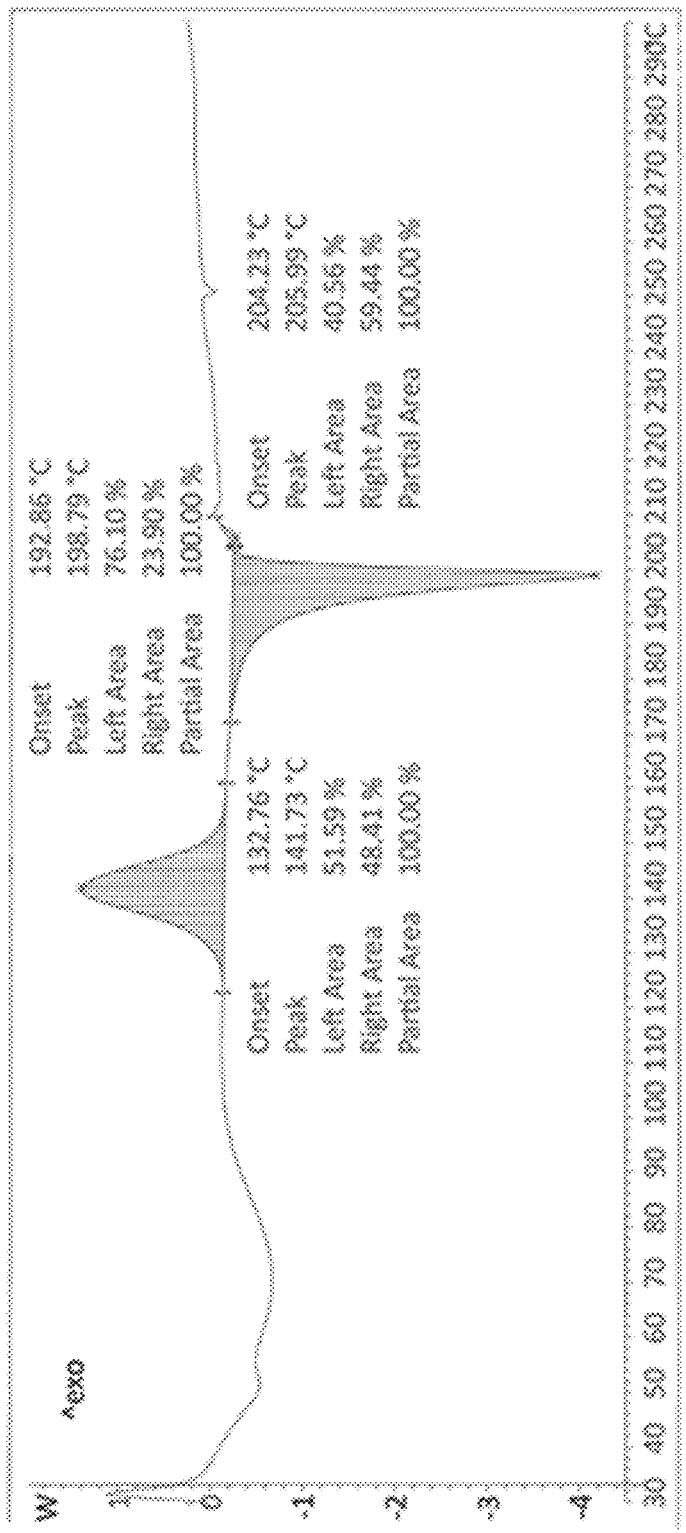
FIG. 5 shows the differential scanning calorimetry (DSC) diagram of the remimazolam besylate obtained in Comparative Example 3.

A product having an amorphous structure was obtained only in one case, in assay 3.2. The solid obtained had amorphous structure with trace contamination of crystalline forms, as can be verified by the presence of signals at 15.8 and 16.2 degrees 2θ in the X-ray diffraction pattern of FIG. 4, corresponding to form 2 of document WO 2008/007071 A1. The DSC of this solid is reproduced in FIG. 5. In the DSC, the presence of amorphous form is clearly seen through the exotherm present in the range between 130 and 140° C., corresponding to the crystallization process of said form upon being heated. The subsequent endotherms correspond to the melting of crystalline forms 1 and 3 and the endotherm of form 2 should appear shortly before (180° C.) the endotherm of form 1 (190° C.); however, in this case a rather broad endotherm is observed, making it difficult to form a conclusion concerning the presence of crystalline form 2 present as contamination of the amorphous form by means of said technique. Nevertheless, contamination with crystalline forms was clearly observed in the X-ray diffraction pattern, as indicated above.

Comparative Example 4. Reproducing the Obtainment of the Amorphous Form from the Polymorphism Study of Example 5 of Patent EP2081921B1

To reproduce the obtention of the amorphous form as indicated in entries 3, 5, and 17 of Table 11 (page 12 of European patent EP 2 081 921 B1), the following experiments considered as representative of the description disclosed in Example 5, polymorphism study, of the mentioned European patent, were performed.

Three different samples weighing 5 g each corresponding to crystalline form 1 of remimazolam besylate (form 1 according to document WO 2008/007071 A1) were mixed at a temperature of about 20° C. with 10 mL of isopropanol (assay 4.1), 10 mL of dichloromethane (assay 4.2), and 10 mL of a mixture of THF and 2.5% of water (V/V) (assay 4.3), respectively. The 3 mixtures thus obtained were subjected to the following cycle performed consecutively for 172 hours by means of a Mettler Toledo EasyMax 102 apparatus:
  a) heating at a temperature of 60-62° C. in 30 minutes,
  b) maintaining at a temperature of 60-62° C. for 10 minutes,
  c) cooling to a temperature of 20-25° C. in 15 minutes,
  d) maintaining at a temperature of 20-25° C. for 10 minutes.

Once the indicated cycles ended, the solvent of each of the three obtained mixtures was evaporated in a rotary evaporator with a bath temperature of about 35° C. and the 3 resulting solids were analyzed by means of XRPD and UHPLC.

Figure 6:
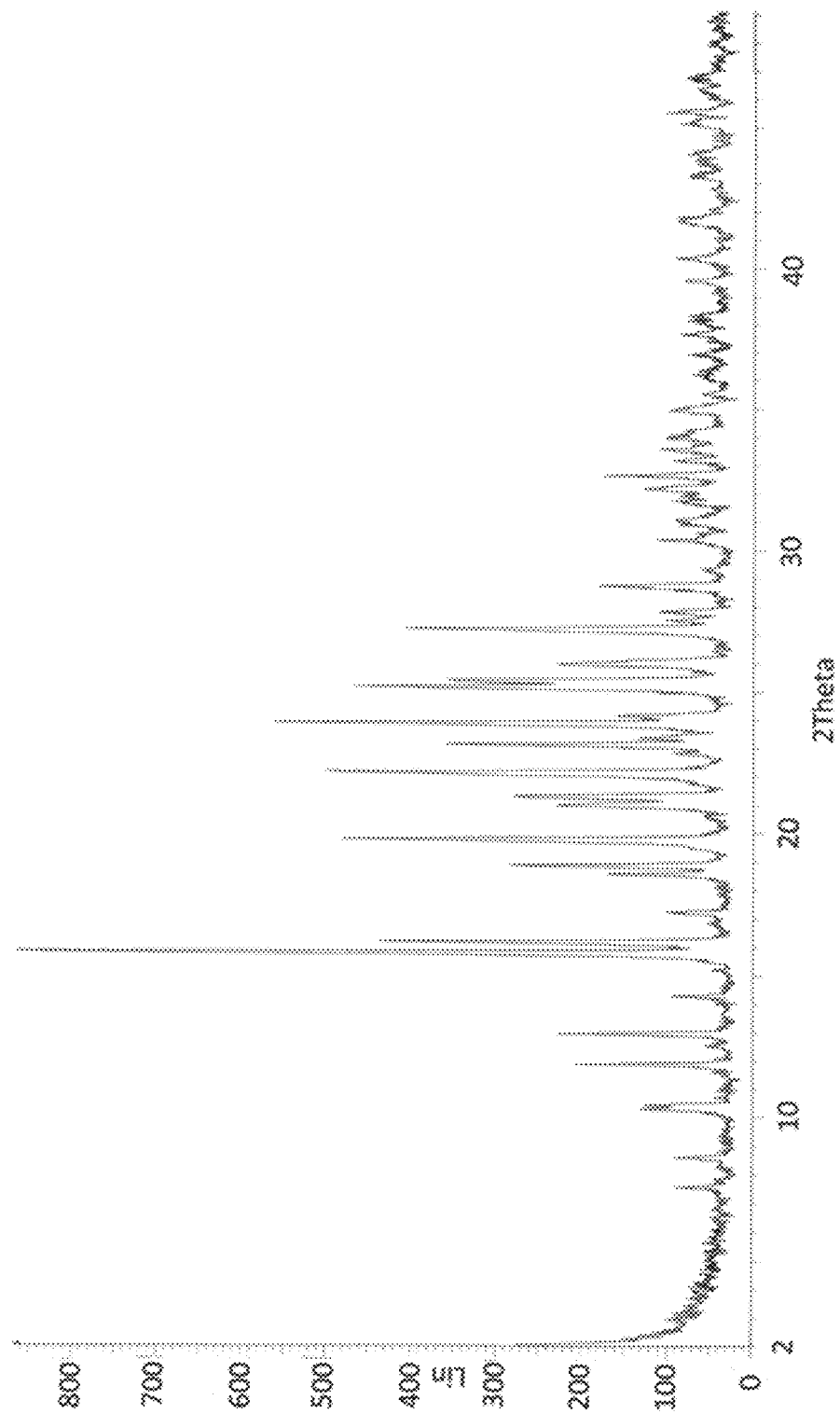
FIG. 6 shows the X-ray powder diffractogram (XRPD) of the remimazolam besylate obtained in Comparative Example 4.1.
Figure 7:
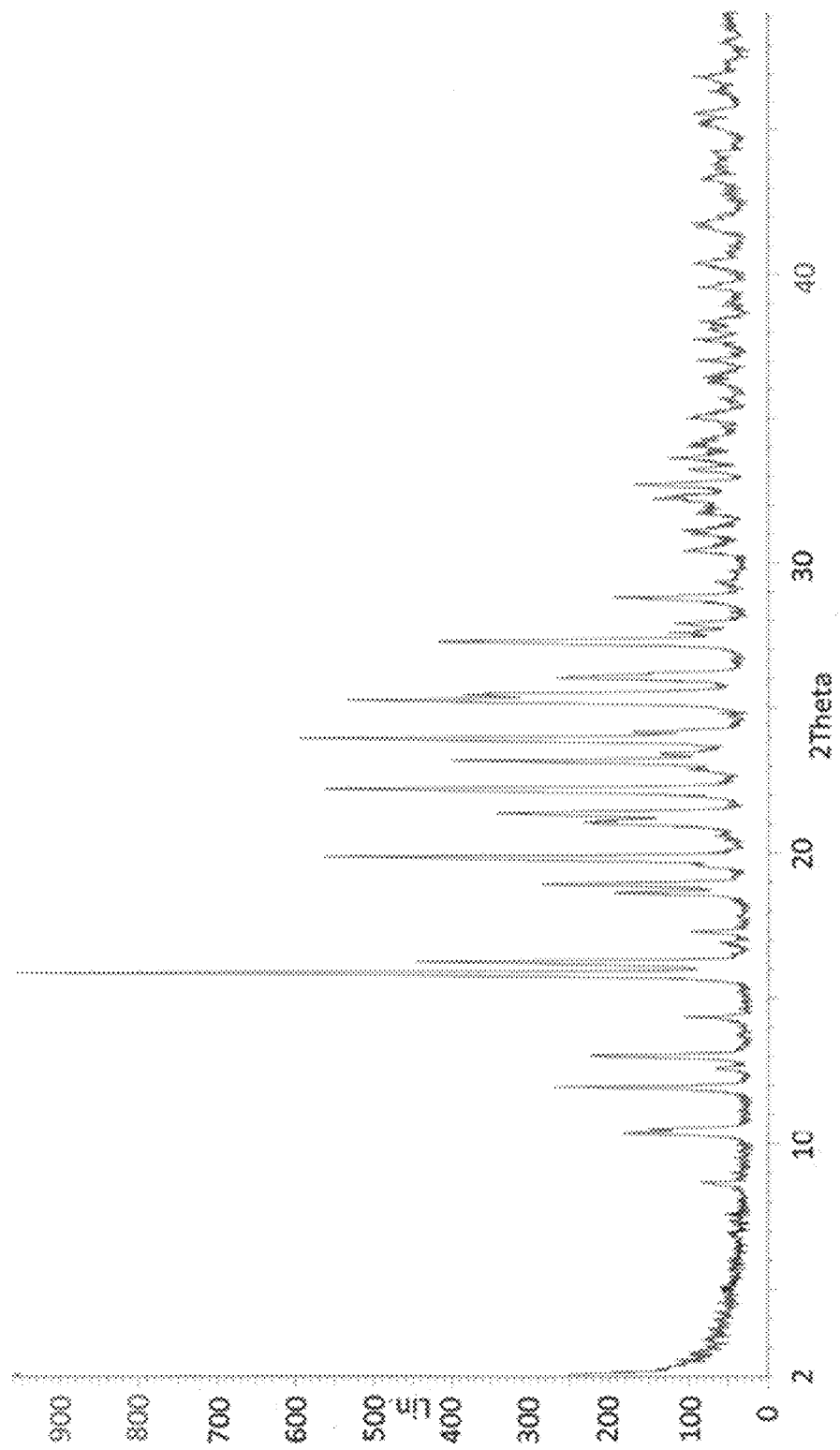
FIG. 7 shows the X-ray powder diffractogram (XRPD) of the remimazolam besylate obtained in Comparative Example 4.2.
Figure 8:
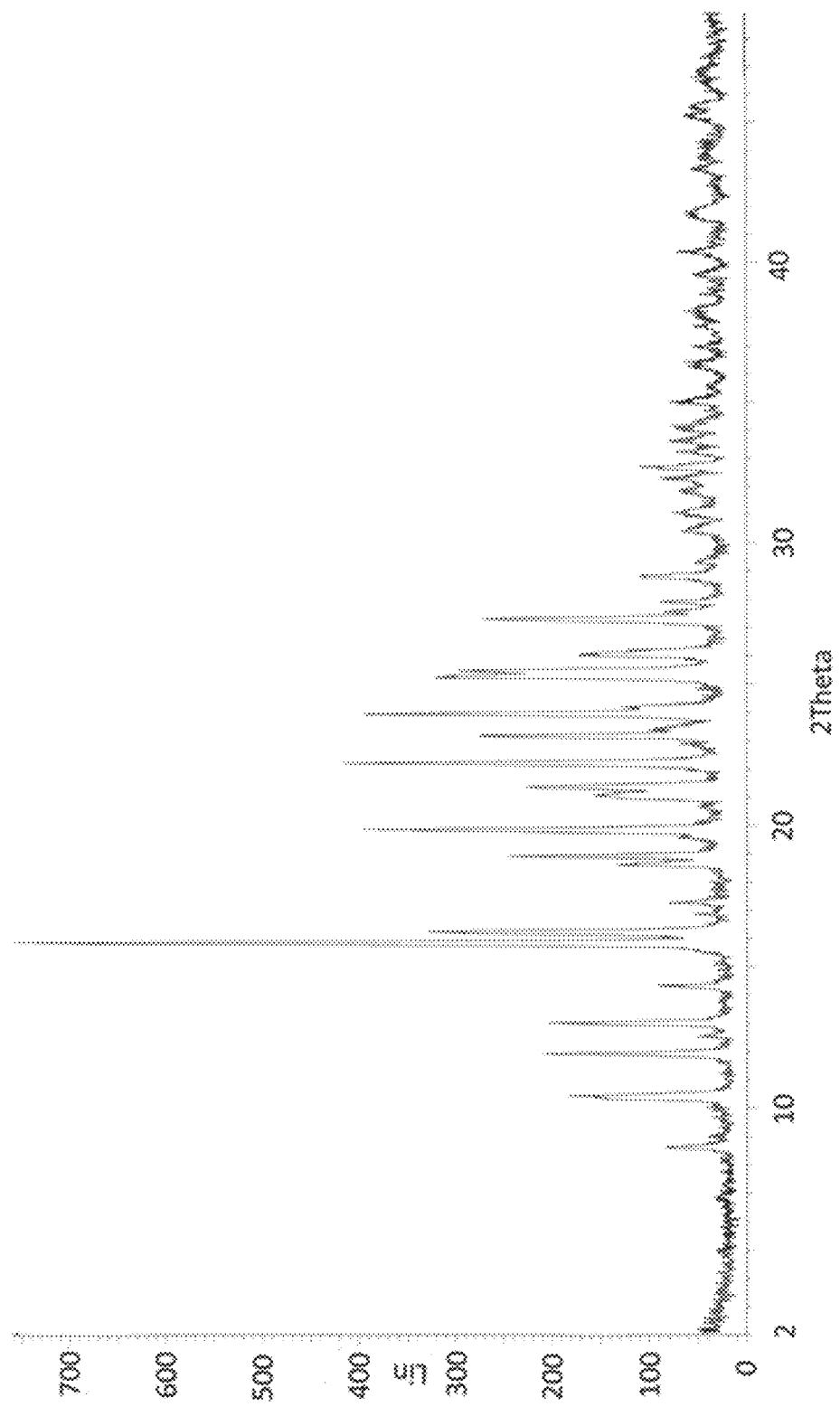
FIG. 8 shows the X-ray powder diffractogram (XRPD) of the remimazolam besylate obtained in Comparative Example 4.3.

The three assays led to the obtention of crystalline form 2 of remimazolam besylate (form 2 according to document WO 2008/007071 A1), without the presence of the amorphous form of said salt being observed, as can be seen in the XRPD of the solids obtained in each of assays 4.1 (FIG. 6), 4.2 (FIG. 7), and 4.3 (FIG. 8). The UHPLC analysis disclosed the following purity for the obtained products, wherein RM refers to remimazolam and RM-acid refers to the carboxylic acid product obtained by means of remimazolam methyl ester hydrolysis:
  Test 4.1: Remimazolam: 99.64%; RM-acid: 0.22%
  Test 4.2: Remimazolam: 99.74%; RM-acid: 0.17%
  Test 4.3: Remimazolam: 90.92%; RM-acid: 8.53%

Example 5. Stability Study

Figure 9:
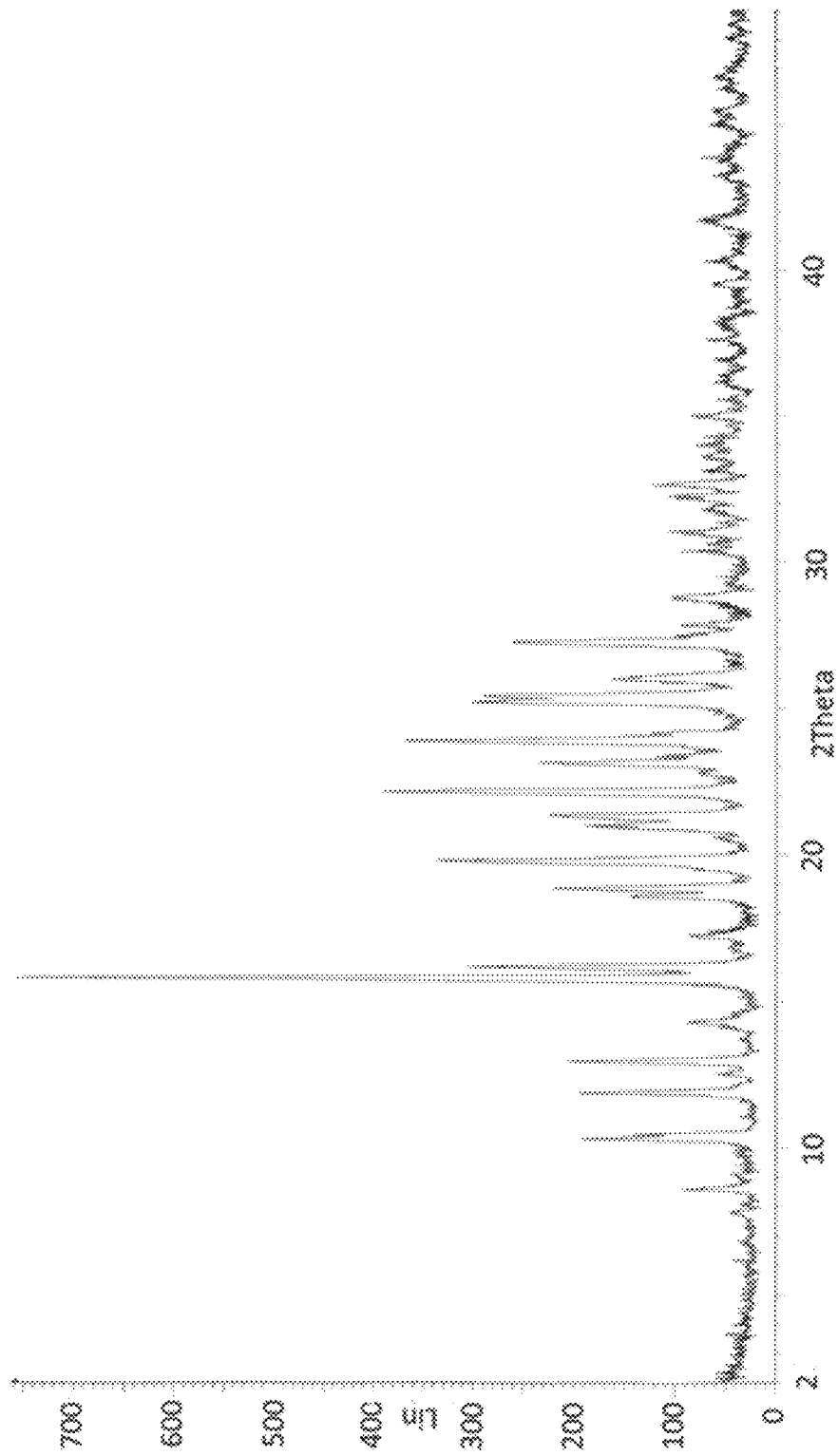
FIG. 9 shows the X-ray powder diffractogram (XRPD) of the remimazolam besylate obtained in Comparative Example 3 after one week of storage at 40° C. and 80% RH.
Figure 10:
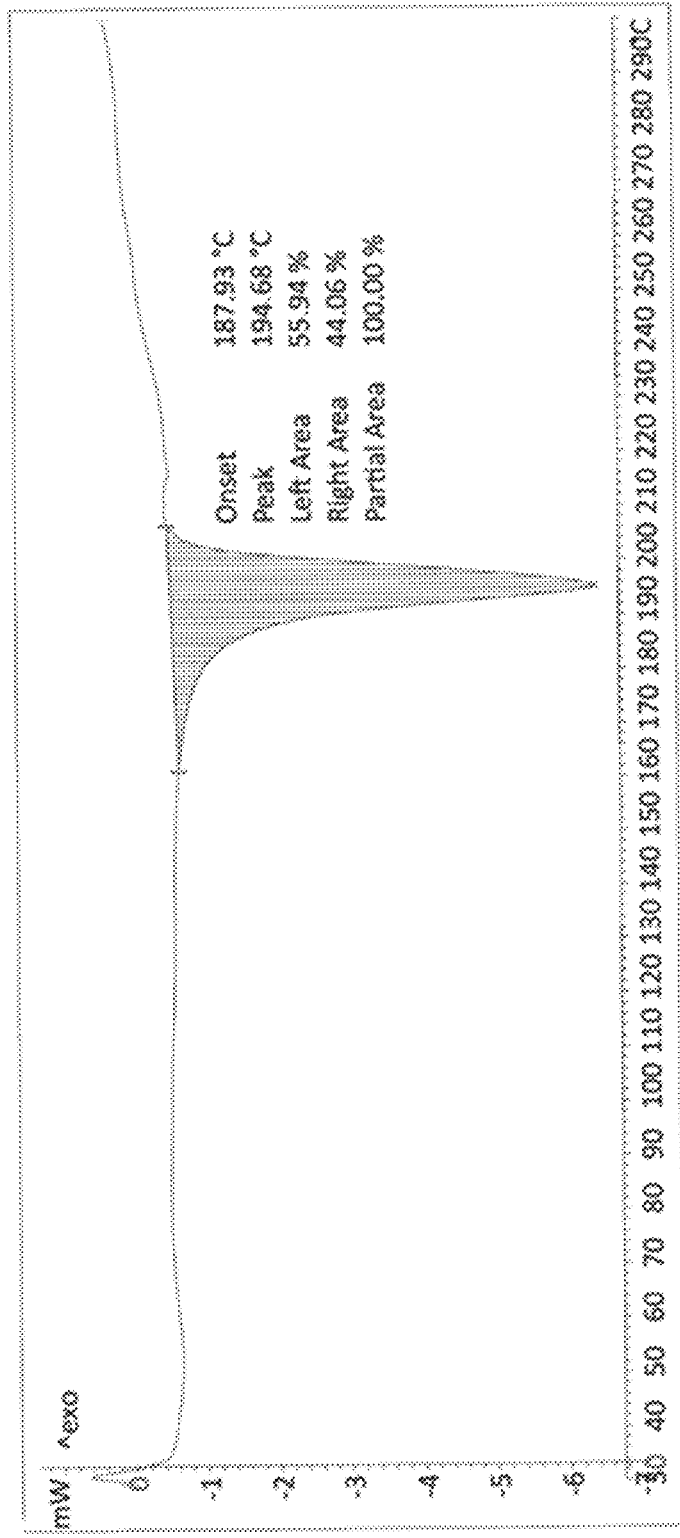
FIG. 10 shows the differential scanning calorimetry (DSC) diagram of the remimazolam besylate obtained in Comparative Example 3 after one week of storage at 40° C. and 80% RH.

The remimazolam besylate obtained in Comparative Example 3 (amorphous form contaminated with traces of crystalline form 2) was stored at 40° C. and 80% RH. After one week of storage under these conditions, the crystalline form 2 described in document WO 2008/007071 A1 is obtained, without the presence of the initial form being observed, as can be seen in the XRPD (FIG. 9) and DSC (FIG. 10).

Figure 11:
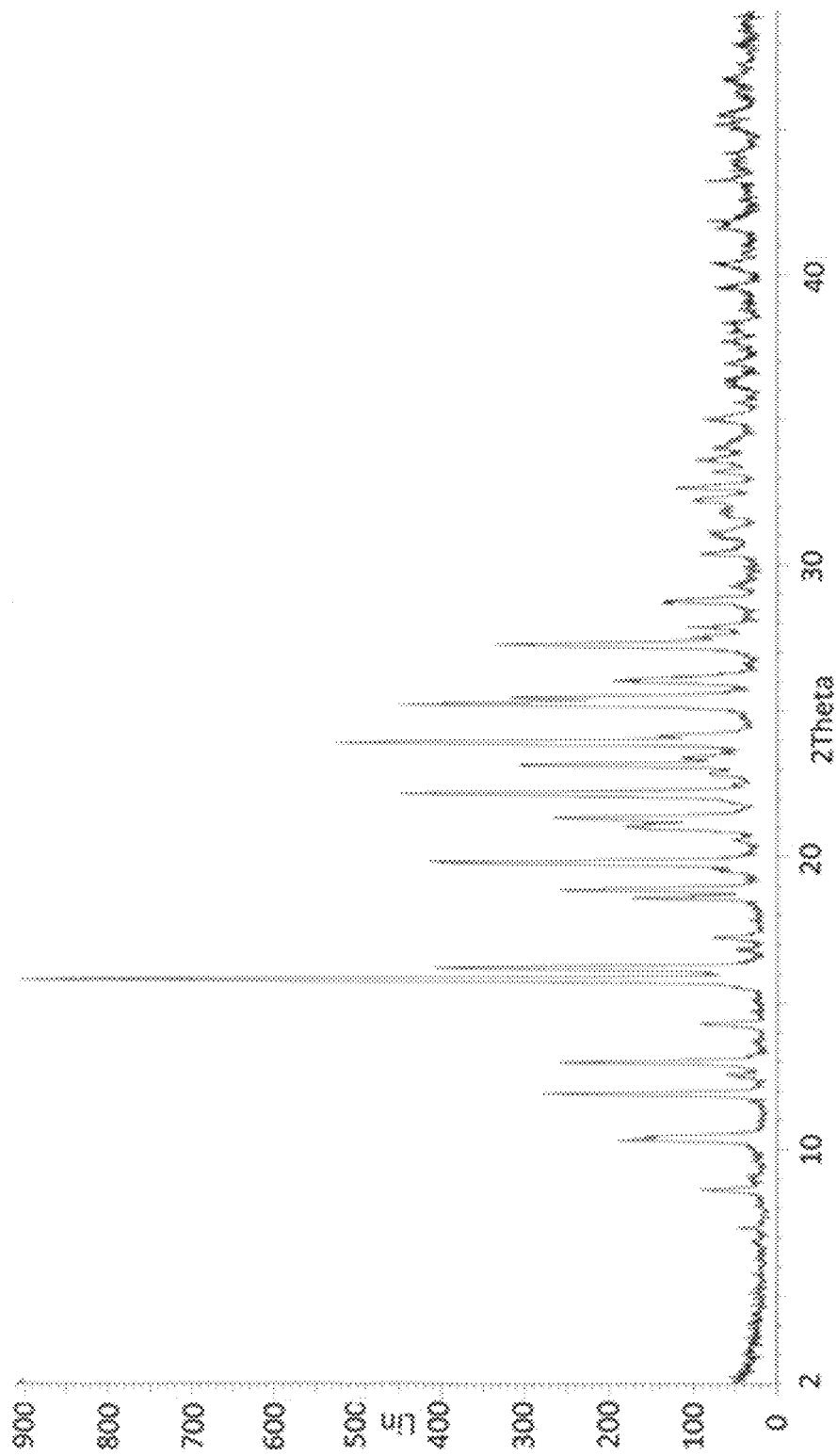
FIG. 11 shows the X-ray powder diffractogram (XRPD) of the remimazolam besylate obtained in Comparative Example 3 after one month of storage at 4° C.
Figure 12:
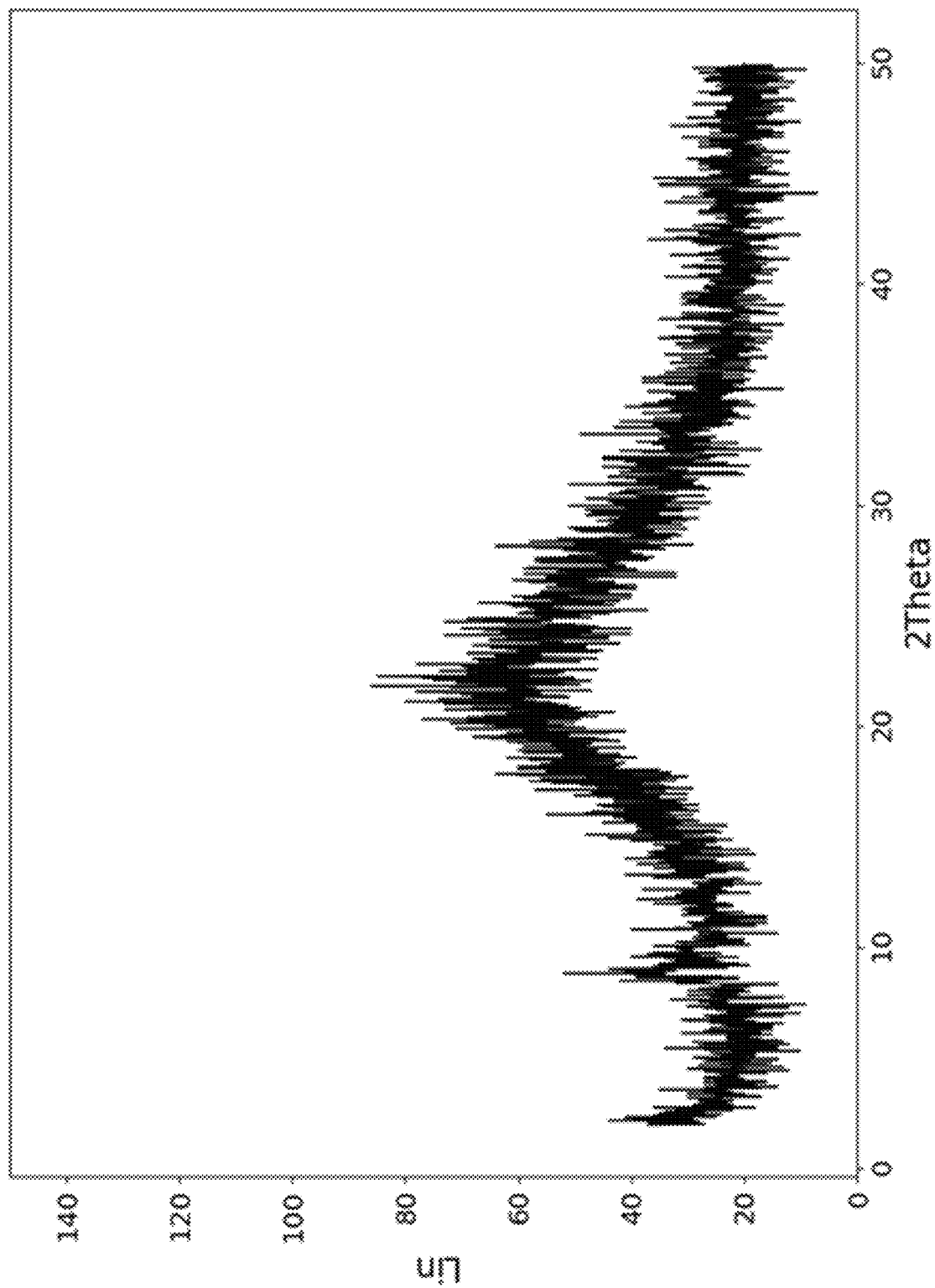
FIG. 12 shows the X-ray powder diffractogram (XRPD) of the remimazolam besylate obtained in assay 1.5 after 15 days of storage at 40° C. and 80% RH.
Figure 13:
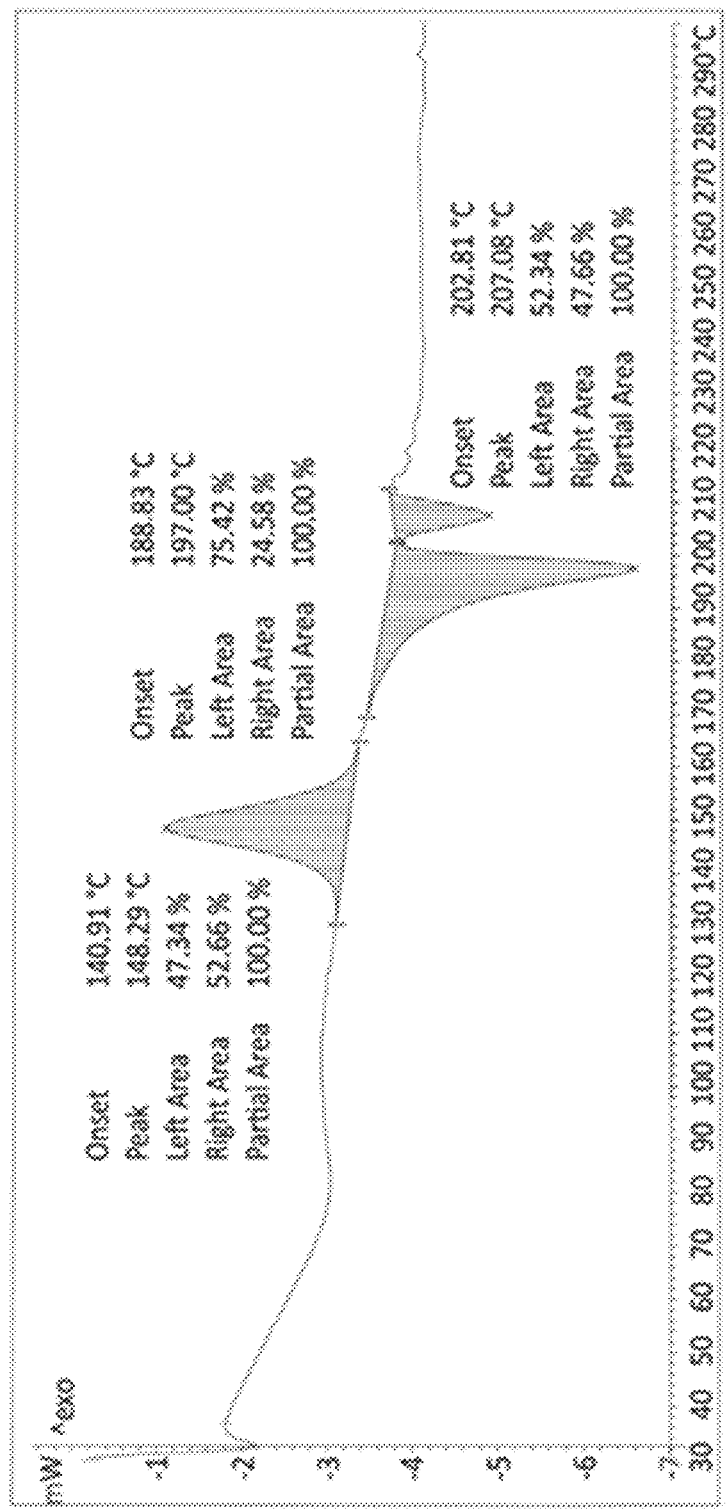
FIG. 13 shows the differential scanning calorimetry (DSC) diagram of the remimazolam besylate obtained in assay 1.5 after 15 days of storage at 40° C. and 80% RH.
Figure 14:
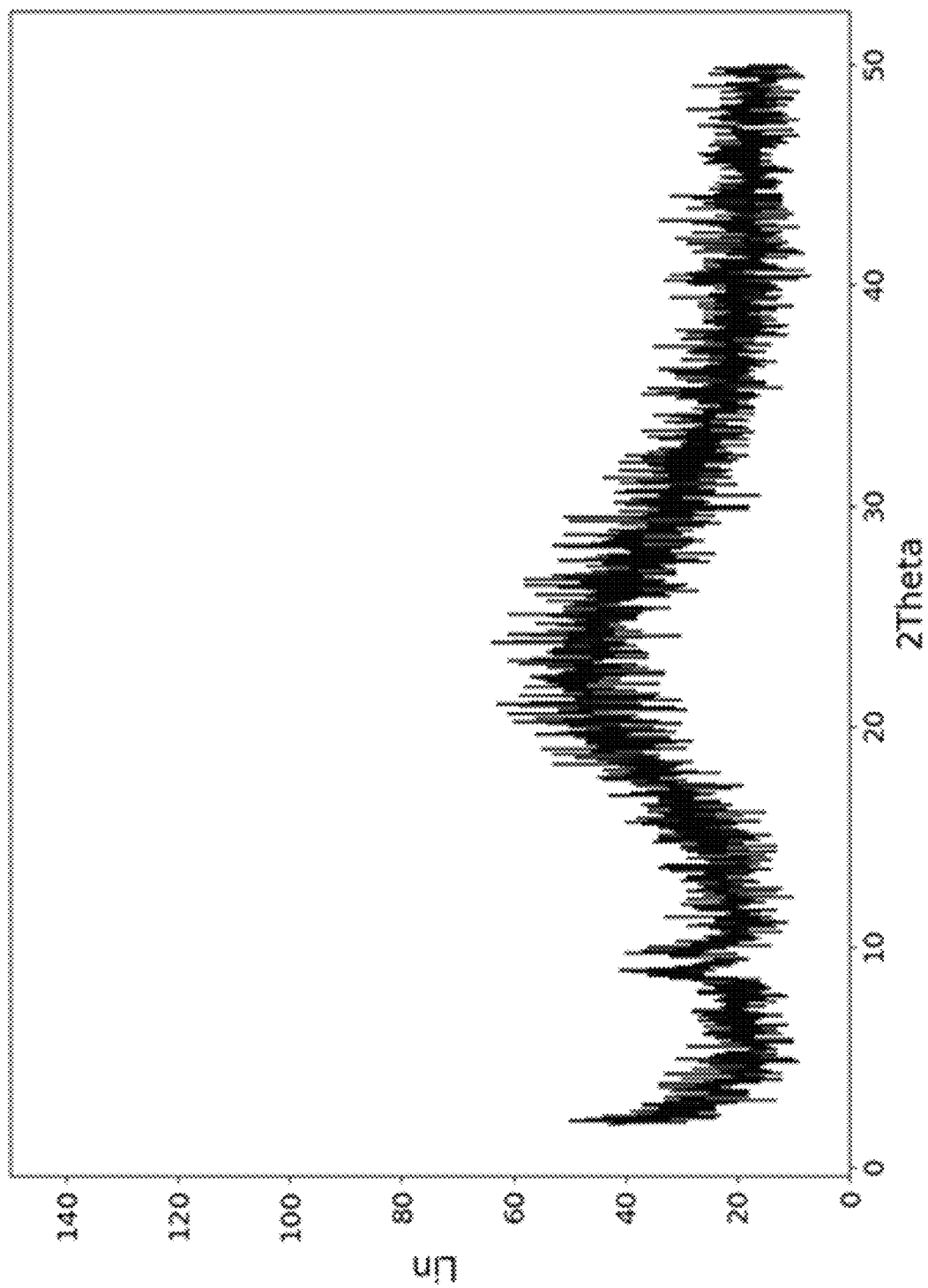
FIG. 14 shows the X-ray powder diffractogram (XRPD) of the remimazolam besylate obtained in assay 1.6 after 15 days of storage at 40° C. and 80% RH.
Figure 15:
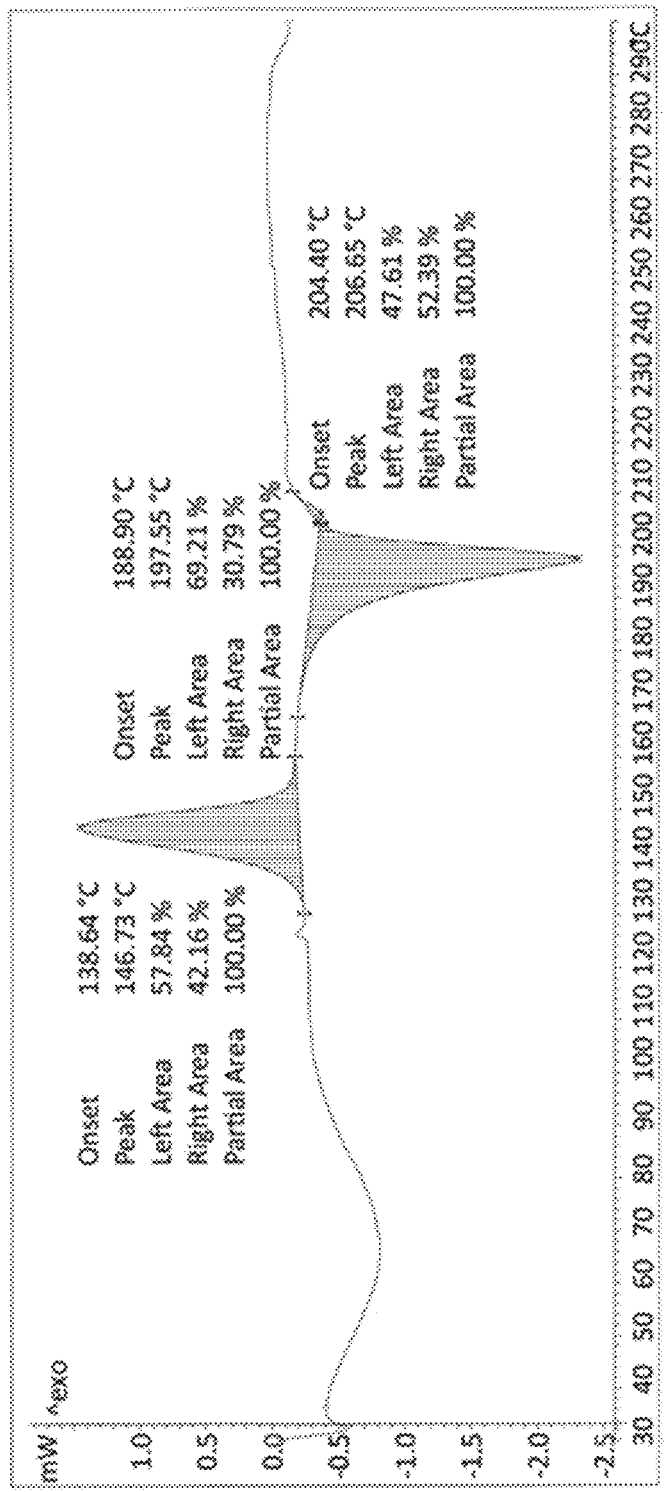
FIG. 15 shows the differential scanning calorimetry (DSC) diagram of the remimazolam besylate obtained in assay 1.6 after 15 days of storage at 40° C. and 80% RH.
Figure 16:
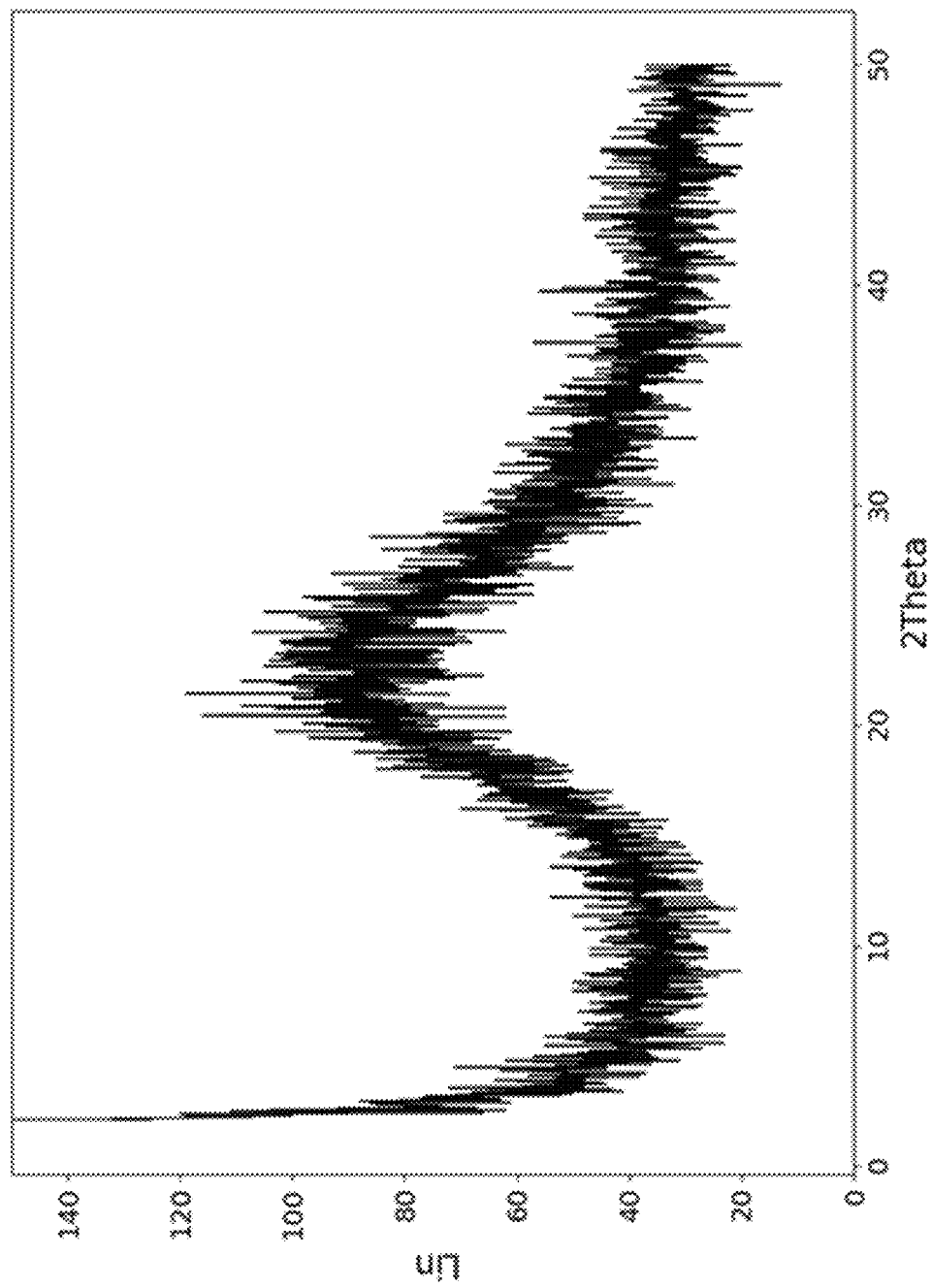
FIG. 16 shows the X-ray powder diffractogram (XRPD) of the remimazolam besylate obtained in assay 1.5 after 30 days of storage at 40° C. and 80% RH.
Figure 17:
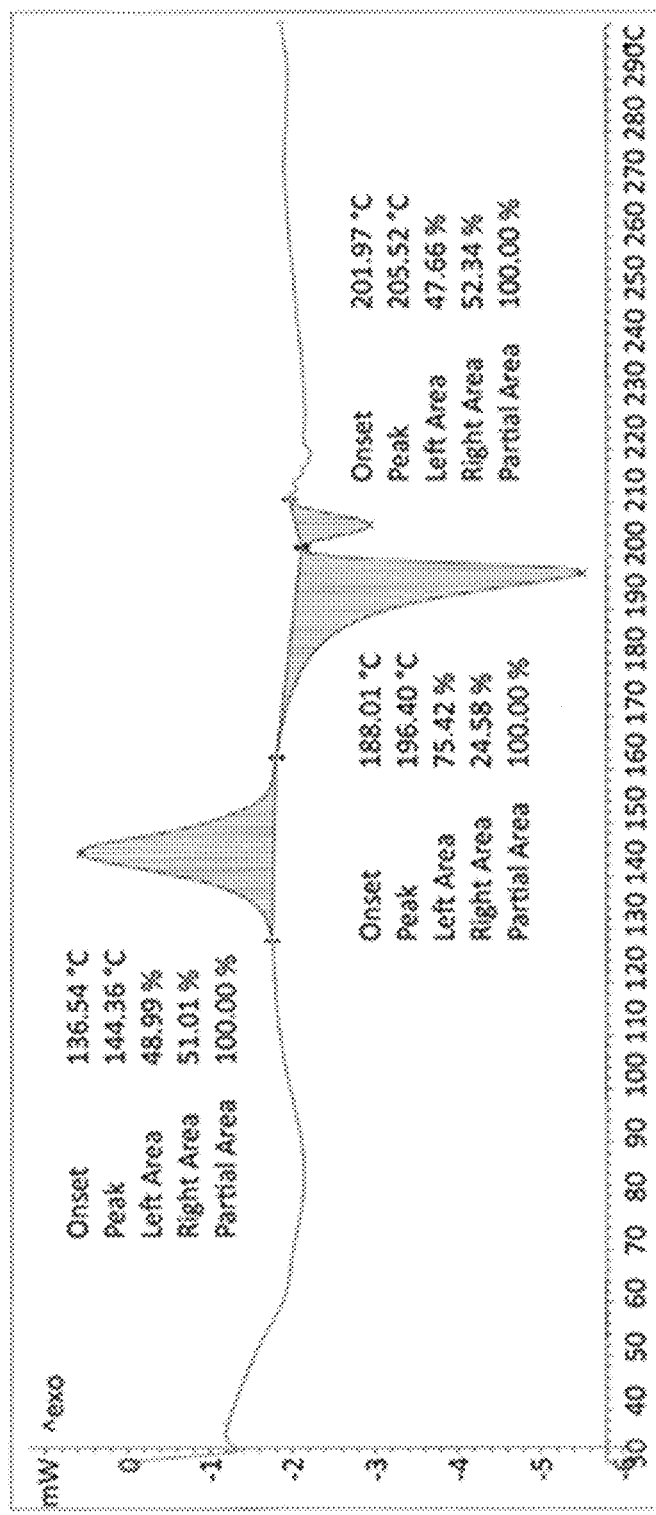
FIG. 17 shows the differential scanning calorimetry (DSC) diagram of the remimazolam besylate obtained in assay 1.5 after 30 days of storage at 40° C. and 80% RH.
Figure 18:
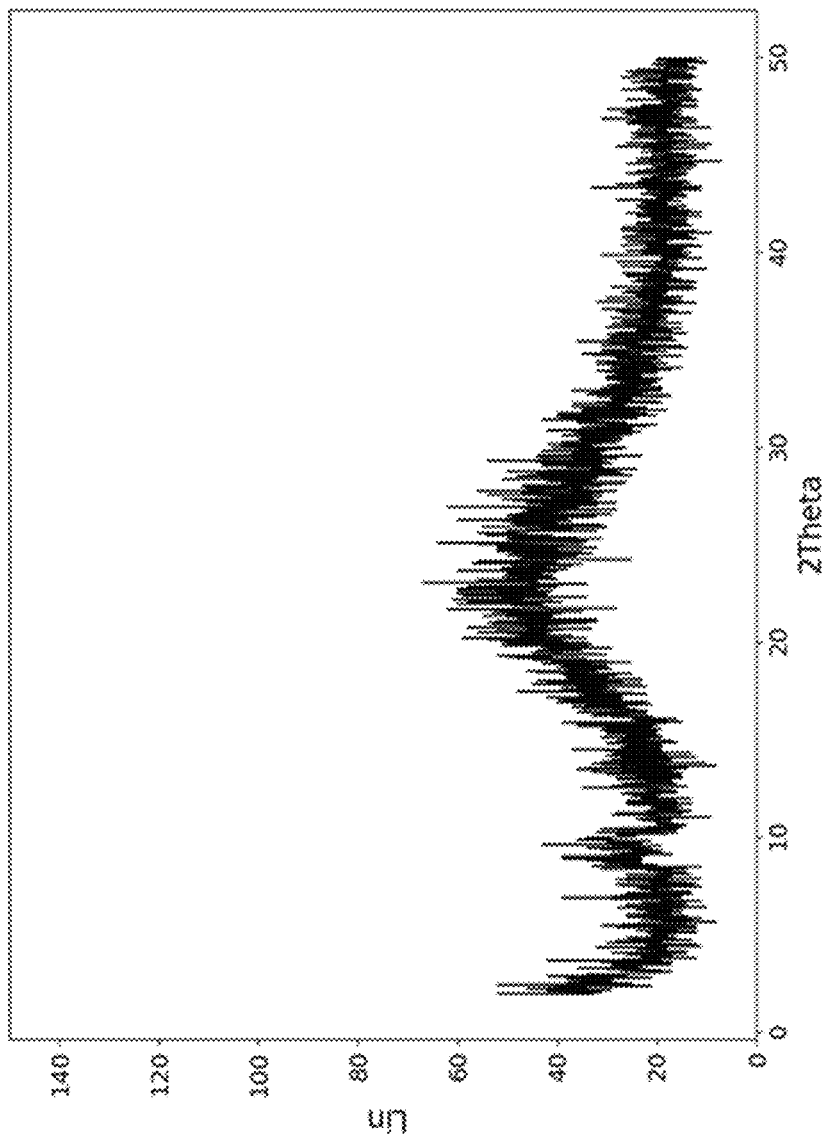
FIG. 18 shows the X-ray powder diffractogram (XRPD) of the remimazolam besylate obtained in assay 1.6 after 30 days of storage at 40° C. and 80% RH.
Figure 19:
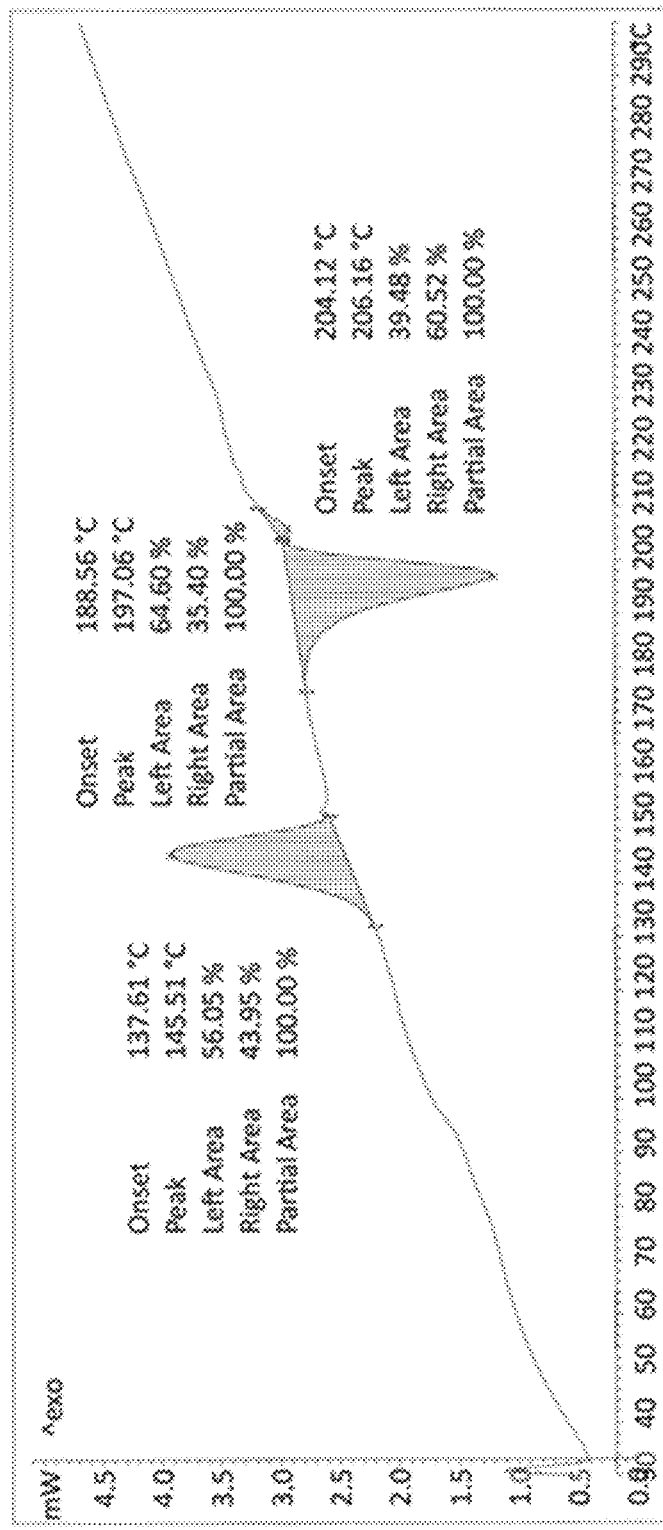
FIG. 19 shows the differential scanning calorimetry (DSC) diagram of the remimazolam besylate obtained in assay 1.6 after 30 days of storage at 40° C. and 80% RH.

The remimazolam besylate obtained in Comparative Example 3 (amorphous form contaminated with traces of crystalline form 2) was also stored at 4° C. After one month of storage under these conditions, the crystalline form 2 described in document WO 2008/007071 A1 is obtained, without the presence of the initial form being observed, as can be seen in the XRPD (FIG. 11).

Figure 20:
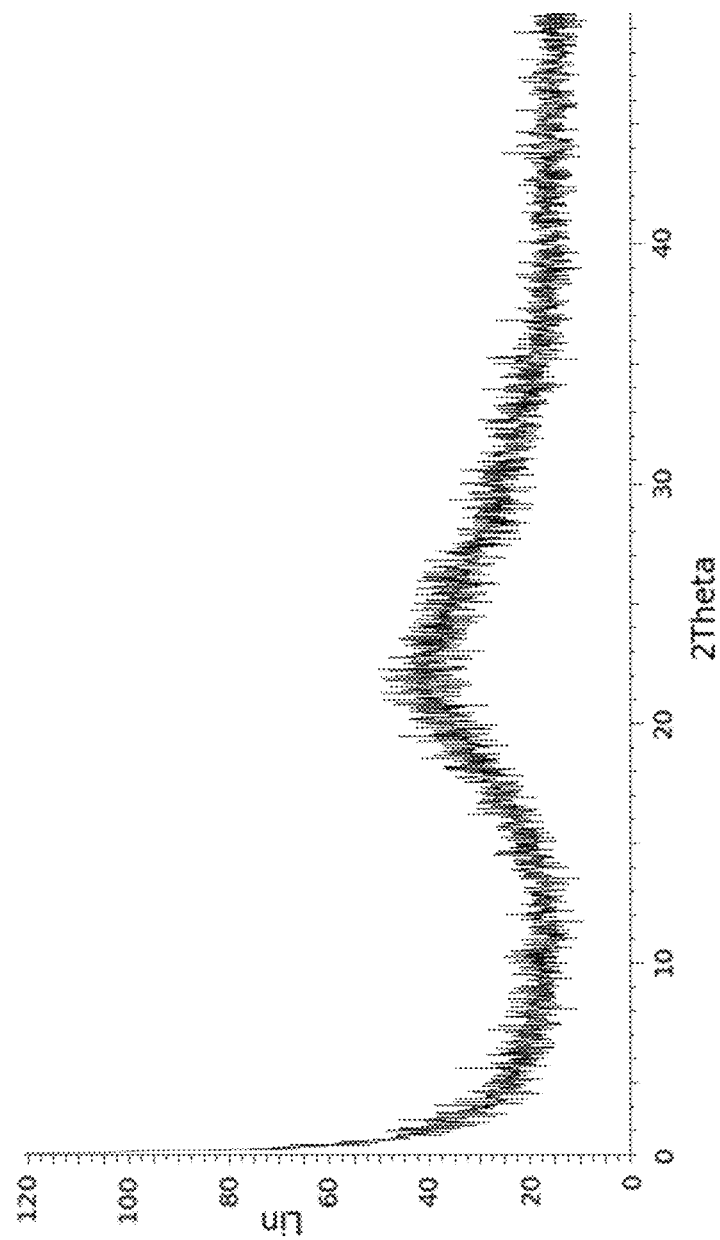
FIG. 20 shows the X-ray powder diffractogram (XRPD) of the remimazolam besylate obtained in assay 1.5 after 6 months of storage at 40° C. and 80% RH.
Figure 21:
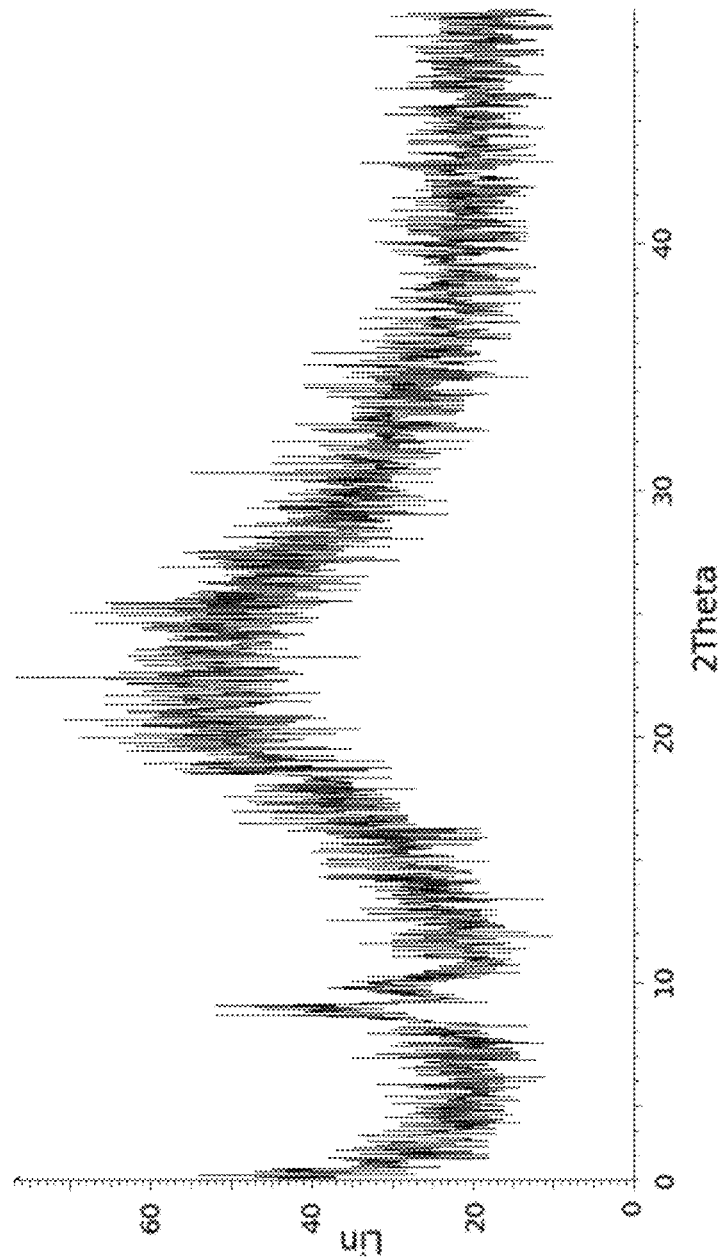
FIG. 21 shows the X-ray powder diffractogram (XRPD) of the remimazolam besylate obtained in assay 1.6 after 6 months of storage at 40° C. and 80% RH.

However, when remimazolam besylate in amorphous form is obtained without the presence of crystalline form being observed, said amorphous form is stable over time and does not develop into a crystalline form. This is proven in the stability results of the product in amorphous form obtained according to assays 1.5 (lyophilization in acetonitrile) and 1.6 (lyophilization in water) indicated in Table 1. To determine said stability, the product was stored in climatic chambers under two different conditions: a) temperature of 40° C. and 80% relative humidity and b) temperature of 25° C. and 60% relative humidity. The product stored under the conditions a) for 15 days and 30 days still maintains the initial characteristics in terms of the amorphous form, as shown in the XRPD and DSC patterns determined after the mentioned 15 days (FIGS. 12 to 15) as well as after the mentioned 30 days (FIGS. 16 to 19). The product stored under the conditions a) for 6 months still maintains the initial characteristics in terms of the amorphous form, as shown in the XRPD patterns determined after the mentioned 6 months (FIGS. 20 and 21).

The invention claimed is:

1. A method for preparing amorphous remimazolam besylate comprising the following steps:
  a) providing a solution consisting essentially of remimazolam besylate and a solvent selected from the group consisting of water-miscible organic solvent, water, and mixtures thereof, and
  b) lyophilizing the solution provided in step a), wherein the lyophilization comprises
    b1) freezing the solution provided in step a) at a temperature below −45° C., and
    b2) removing the solvent from the product obtained in step b1) by means of heating from the temperature of said product to a temperature of 10° C. to 40° C., at a pressure of less than 101325 Pa and for a time period of less than 5 days.

2. The method according to claim 1, wherein the solvent of the remimazolam besylate solution provided in step a) is selected from the group consisting of water, acetonitrile, and mixtures thereof.

3. The method according to claim 1, wherein the concentration of remimazolam besylate in the solution provided in step a) is 5 to 15 mg/mL.

4. The method according to claim 1, wherein the freezing temperature of step b1) is below −55° C.

5. The method according to claim 4, wherein the freezing temperature of step b1) is from −55° C. to −85° C.

6. The method according to claim 5, wherein the freezing temperature of step b1) is from −55° C. to −65° C. or from −75° C. to −85° C.

7. The method according to claim 1, wherein temperature of step b1) is maintained for 10 minutes to 36 hours.

8. The method according to claim 7, wherein the temperature of step b1) is maintained for 10 minutes to 1 hour or for 15 hours to 30 hours.

9. The method according to claim 1, wherein the freezing temperature of step b1) is from −55° C. to −65° C. and is maintained at this temperature range for 15 hours to 30 hours, or wherein the freezing temperature of step b1) is from −75° C. to −85° C. and is maintained at this temperature range for 10 minutes to 1 hour.

10. The method according to claim 1, wherein the pressure in step b2) is 0.01 Pa to 101000 Pa.

11. The method according to claim 10, wherein the pressure in step b2) is from 0.01 Pa to 100 Pa or 50000 Pa to 101000 Pa.

12. The method according to claim 1, wherein heating in step b2) is performed to a temperature of 15 to 30° C.

13. The method according to claim 1, wherein step b2) is performed for a time period of 20 to 60 hours.

14. The method according to claim 1, wherein step b2) is performed at a pressure of 50000 Pa to 101000 Pa for a time period of 20 to 30 hours.

15. The method according to claim 1, wherein step b2) is performed at a pressure of 0.01 Pa to 100 Pa for a time period of 40 to 60 hours.

16. The method according to claim 15, wherein step b2) comprises:
- (i) maintaining a temperature of −30° C. to −20° C. and a pressure of 10 Pa to 50 Pa for a time period of 15 to 24 h,
- (ii) maintaining a temperature of −5° C. to 5° C. and a pressure of 10 Pa to 50 Pa for a time period of 6 to 18 h,
- (iii) maintaining a temperature of 8° C. to 15° C. and a pressure of 10 Pa to 50 Pa for a time period of 12 to 24 h, or
- (iv) maintaining a temperature of 15° C. to 25° C. and a pressure of 0.01 Pa to 1 Pa for a time period of 3 to 18 h.

17. The method according to claim 1, wherein the temperature variation in step b2) is from 0.5 to 1.5° C./minute.

18. Stable amorphous remimazolam besylate, characterized in that it shows an X-ray powder diffractogram presenting a broad peak between 1° and 40° 2θ±2° 2θ.

* * * * *